(12) United States Patent
Zandi et al.

(10) Patent No.: US 11,957,562 B2
(45) Date of Patent: *Apr. 16, 2024

(54) FILTER APPARATUSES AND METHODS

(71) Applicant: Transverse Medical, Inc., Denver, CO (US)

(72) Inventors: Abdolrahim Zandi, Laguna Niguel, CA (US); J. Eric Goslau, Evergreen, CO (US); Sepehr Fariabi, Newport Coast, CA (US)

(73) Assignee: Transverse Medical, Inc., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/671,013

(22) Filed: Feb. 14, 2022

(65) Prior Publication Data

US 2022/0168086 A1    Jun. 2, 2022

Related U.S. Application Data

(63) Continuation of application No. 16/095,875, filed as application No. PCT/US2018/024560 on Mar. 27, 2018, now Pat. No. 11,246,698.
(Continued)

(51) Int. Cl.
*A61F 2/01* (2006.01)
*A61B 17/00* (2006.01)
*A61B 17/221* (2006.01)

(52) U.S. Cl.
CPC ........ *A61F 2/013* (2013.01); *A61B 17/00234* (2013.01); *A61B 17/221* (2013.01);
(Continued)

(58) Field of Classification Search
CPC ........ A61F 2/01; A61F 2/0103; A61F 2/0108; A61F 2/011; A61F 2/013; A61F 2002/016
See application file for complete search history.

(56) References Cited

U.S. PATENT DOCUMENTS 11,246,698 B2 *   2/2022  Zandi ................... A61B 17/221
2011/0295304 A1 * 12/2011 Jonsson ........... A61B 17/12109
                                                      606/200
(Continued)

FOREIGN PATENT DOCUMENTS

WO      2004/049978 A1    6/2004
WO      2010026240 A1     3/2010
(Continued)

OTHER PUBLICATIONS

EPO. Supplementary Partial European Search Report for counterpart European Patent Application No. 18776442.8 dated Apr. 24, 2019, 6 pgs.
(Continued)

*Primary Examiner* — Todd J Scherbel
(74) *Attorney, Agent, or Firm* — Crawford Maunu PLLC

(57) ABSTRACT

Aspects of the present disclosure are directed toward catheter-based apparatuses, such as componentry utilized with or as part of catheters, or as catheters or catheter assemblies. As may be implemented in accordance with one or more embodiments, a method and/or apparatus involves a filter having a frame that forms a perimeter of the filter and separates opposing surfaces thereof. An articulated arm is connected to the frame and configured therewith to, when deployed within a tubular organ, engage with opposing inner sidewall portions of the tubular organ and to utilize the inner sidewall portions to seal filter to the inner sidewall by applying force to the frame.

20 Claims, 38 Drawing Sheets

Related U.S. Application Data

(60) Provisional application No. 62/476,977, filed on Mar. 27, 2017.

(52) U.S. Cl.
CPC .............. *A61B 2017/00243* (2013.01); *A61B 2017/00292* (2013.01)

(56) References Cited

U.S. PATENT DOCUMENTS

| | | |
|---|---|---|
| 2015/0126997 A1 | 5/2015 | Beetel et al. |
| 2016/0100928 A1 | 4/2016 | Lees et al. |

FOREIGN PATENT DOCUMENTS

| | | |
|---|---|---|
| WO | 2015055605 A1 | 4/2015 |
| WO | 2015177322 A1 | 11/2015 |
| WO | 2017/042808 A1 | 3/2017 |

OTHER PUBLICATIONS

International Search Report and Written Opinion for corresponding application PCT/US2018/024560, dated Jun. 15, 2018.

\* cited by examiner

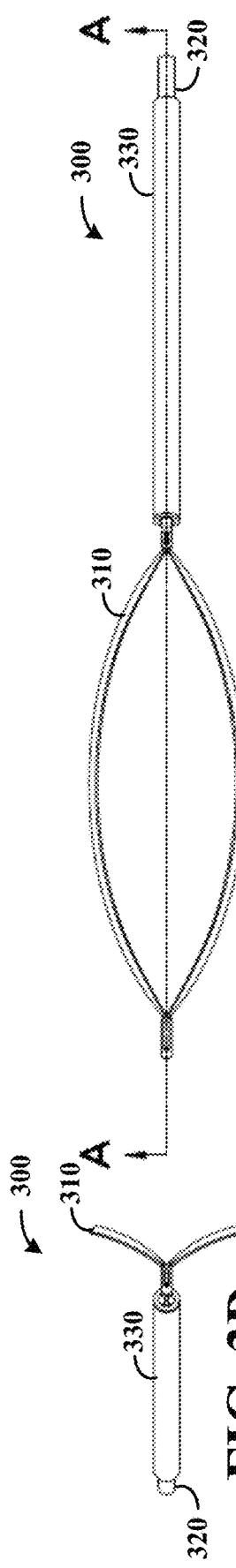
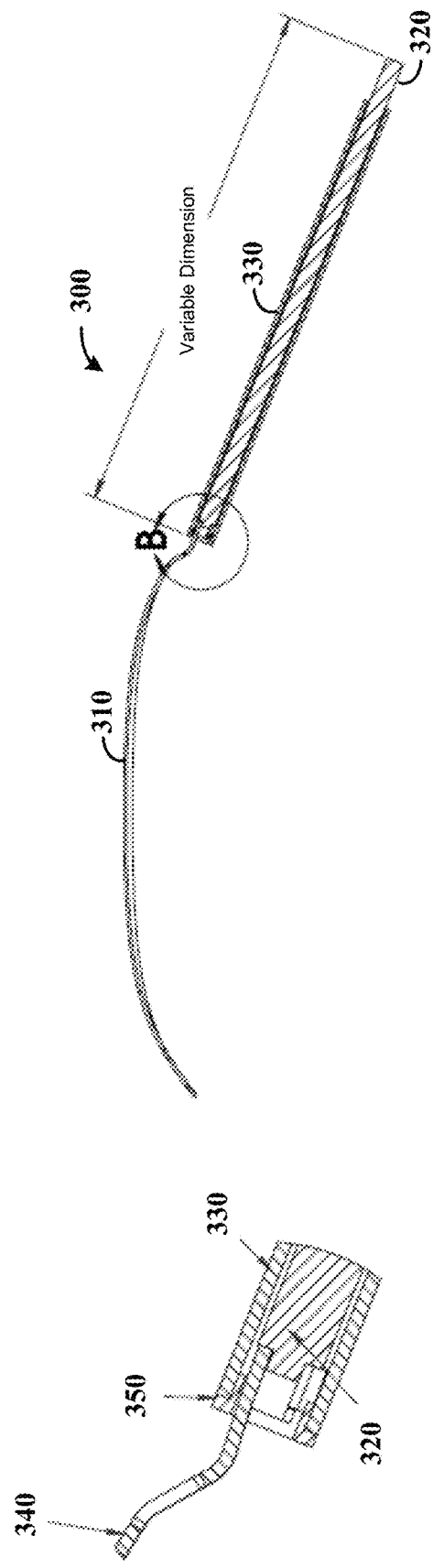

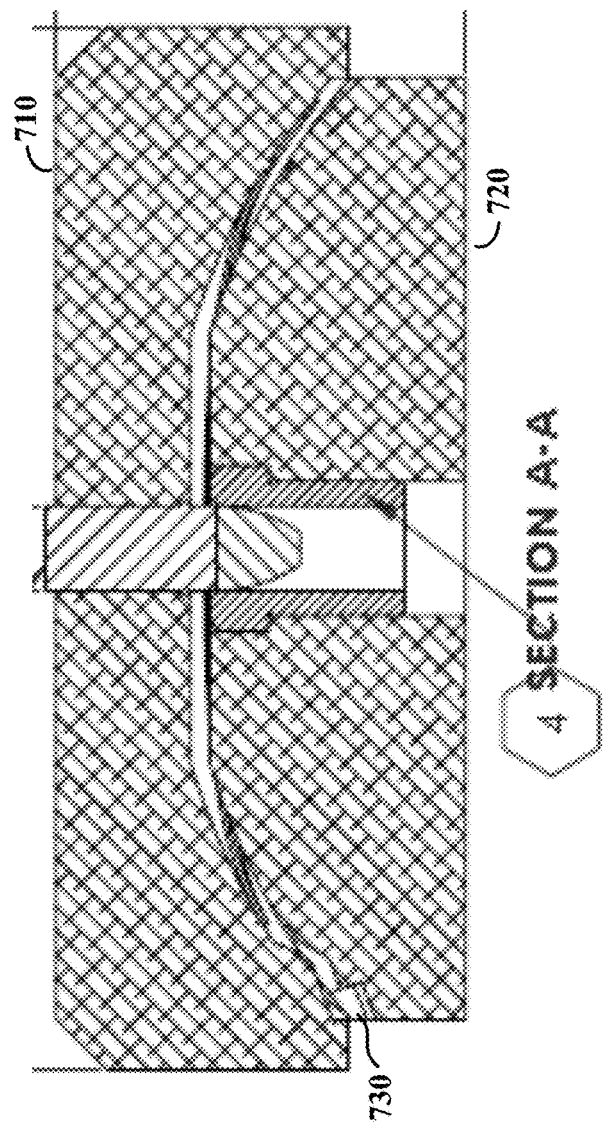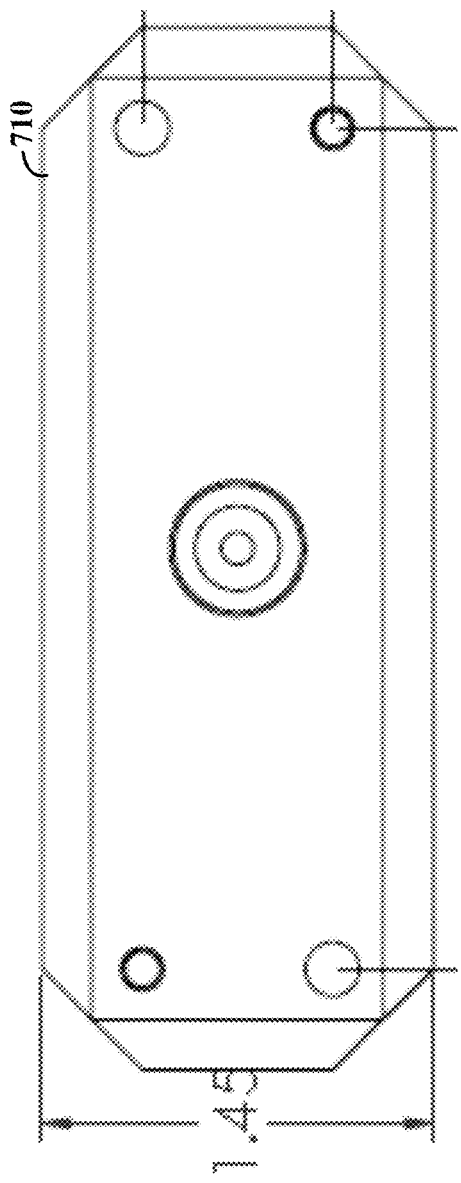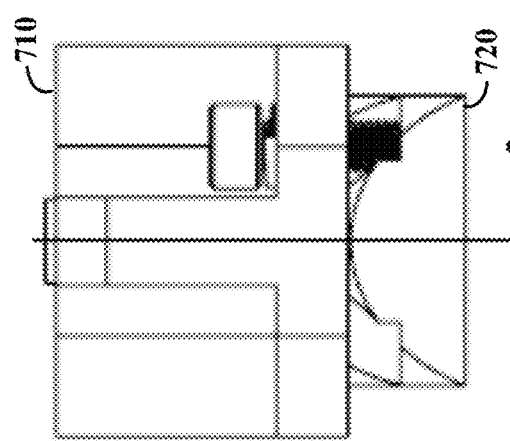
FIG. 7B
FIG. 7C

| | | | |
|---|---|---|---|
| Consolidated Material | Circular, n=1 |  d | 1 |
| | Elliptical, n=5 |  d 5d | 0.72 |
| | Slit, n=10 |  d 10d | 0.71 |
| Fibrous material | Square |  d | 1.0 |
| | Triangular |  d | 1.0 |
| | Rectangular |  d 2d | 0.75 |
FIG. 20

| Average opening size, μm x μm | Shape factor, A | Measured pore diameter, D, μm | Maximum diameter particle that can pass through, d, μm |
|---|---|---|---|
| 45.3 x 45.3 | 1 | 46.2 | 46.2 |
| 81.8 x 81.8 | 1 | 81.2 | 81.2 |
| 7.5 x 20 | 0.7 | 10.1 | 7.1 |

FIG. 21

| | POLYURETHANE | POLYESTER PET | NYLONS | |
|---|---|---|---|---|
| TENSILE STRENGTH | 30-45 | 80 | 185 | Mpa |
| HARDNESS | 70-80 | 84 | 90 | SHORE A |
| SPECIFIC DENSITY | 1.1 | 1.4 | 1.13 | - |
| ELONGATION AT BREAK | 37 | 110 | 340 | % |
| STRESS AT 100% ELONGATION | 4 | 10 | 7 | Mpa |
| TEAR STRENGTH | 40 | 65 | 78 | KN/m |
| MODULUS OF ELASTICITY | 800 | 2700 | 3000 | Mpa |
| RESISTANCE TO BIOFOULING | 2 | 3 | 3 | (1),(2) |
| BIO COMPATIBILTY | 2 | 3 | 3 | (1),(2) |
| FLEXIBILITY | 3 | 2 | 2 | (1),(2) |
| STRETCHABILITY | 4 | 3 | 2 | (1),(2) |
| FOLDABILITY | 3 | 2 | 2 | (1),(2) |
| TWISTABILITY | 4 | 2 | 3 | (1),(2) |
| SELF-BONDING | 4 | 2 | 2 | (1),(2) |

(1): SCALING : 1 TO 4 (POOR TO GOOD)
(2): DEPENDING ON SURFACE TREATMENT

FIG. 27

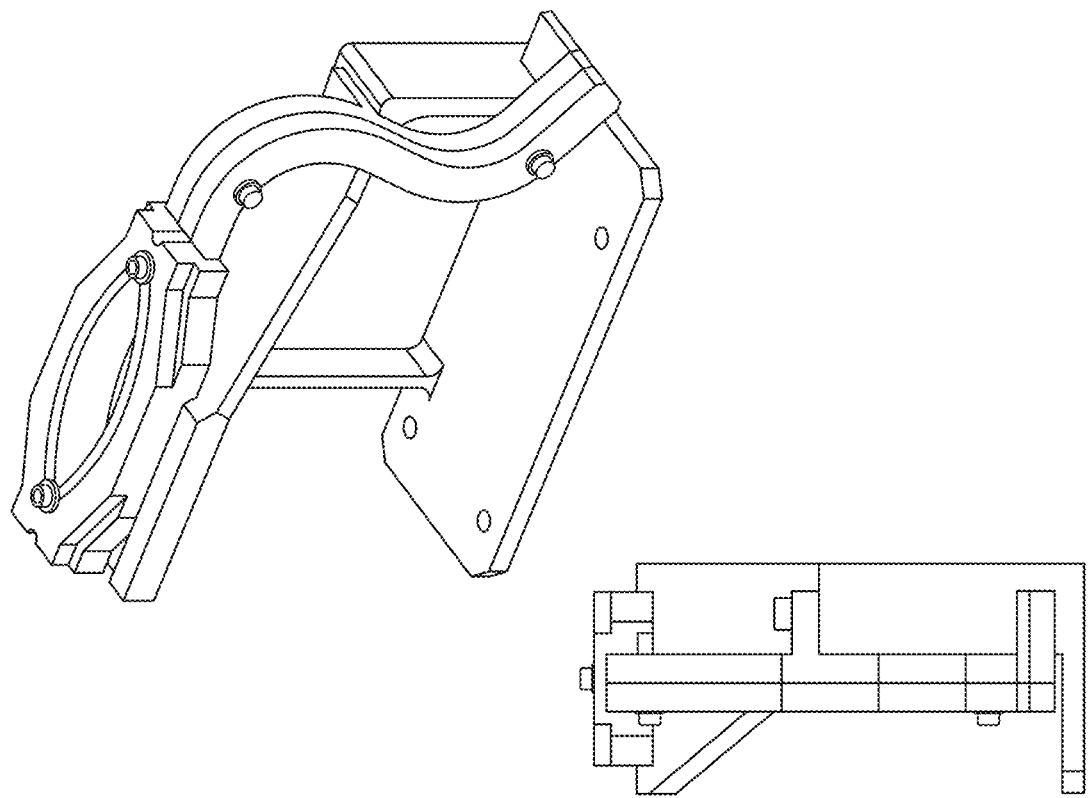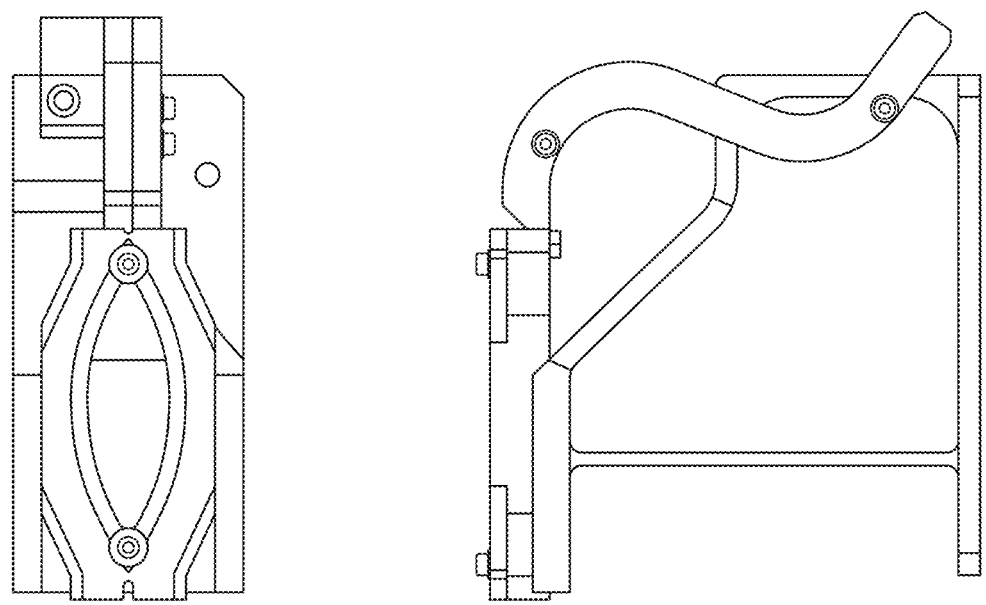
FIG. 28

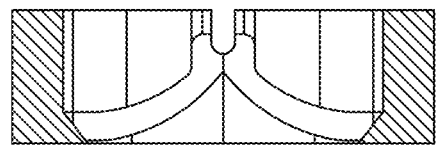
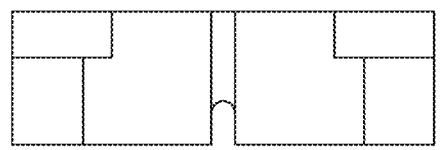
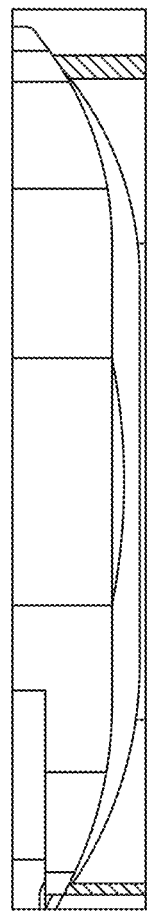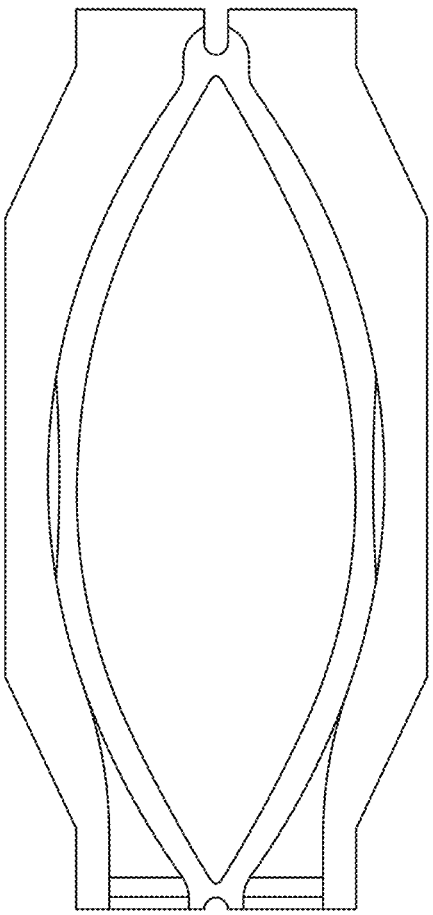
FIG. 31

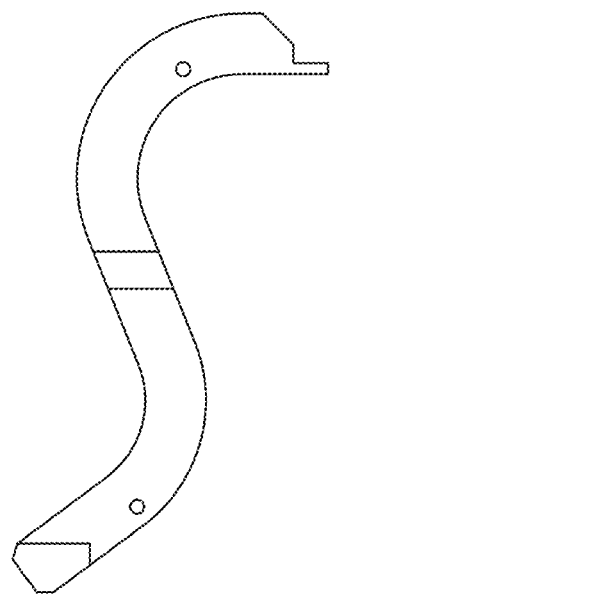
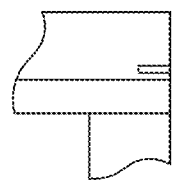
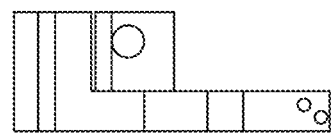
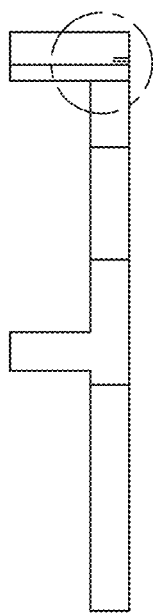
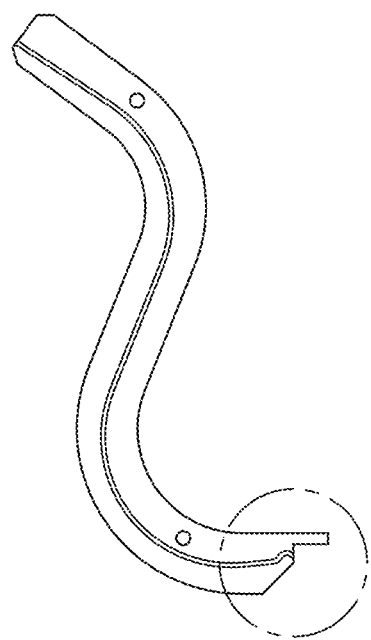
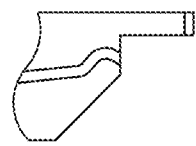
FIG. 34

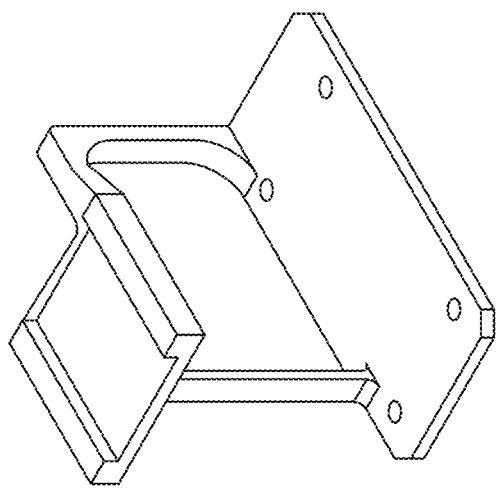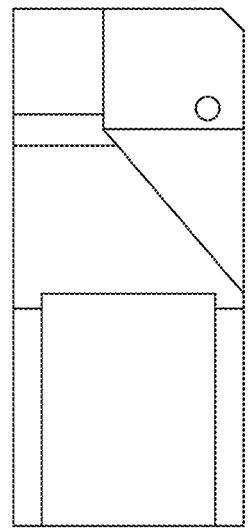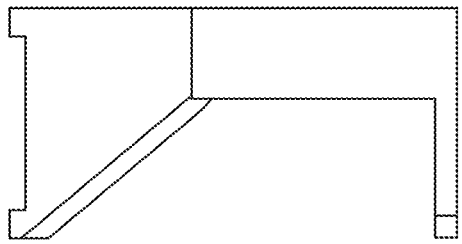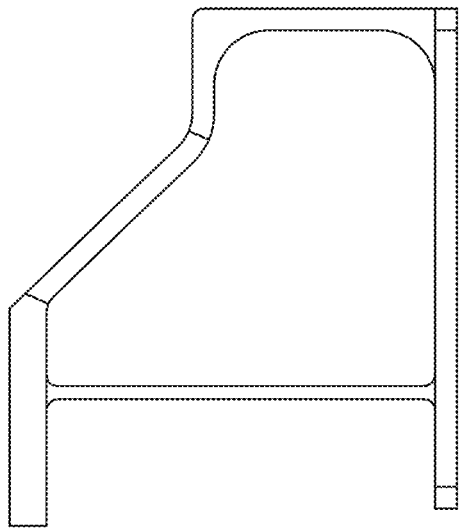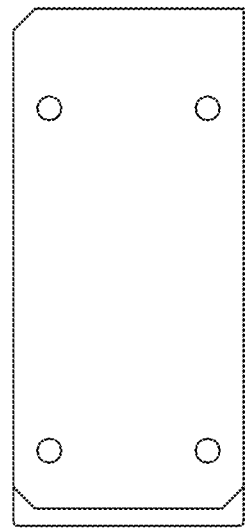
FIG. 35

FILTER APPARATUSES AND METHODS

FIELD

Aspects of various embodiments are directed to catheter-based apparatuses and methods therefor.

OVERVIEW

Various treatments can be useful for treating a variety of medical conditions, such as coronary heart disease, aneurism and others. These treatments can often involve intervention with tissue, such as to remove, repair or otherwise treat tissue. For instance, coronary heart disease can sometimes involve heart valve disorders, which can be addressed via intervention techniques in which valves are repaired or replaced.

One manner that has been useful for treating various conditions involves the use of a catheter to enter a patient's arteries and provide access for a variety of techniques. For instance, various procedures can be performed via catheters, such as to repair or remove tissue, or to implant tissue or other devices. One such approach for addressing heart disease involves transcatheter-aortic valve replacement or implementation therapies (TAVR/TAVI). These and other trans-vascular approaches may involve the delivery of artificial or animal flaps/valves to a patient's heart via catheters.

While many treatment approaches have been useful, there have been many challenges to their safe implementation. It is common to introduce, cross and exchange a variety of percutaneous devices such as guide wires, catheters, sheaths, guide catheters, and adjunctive technologies to gain access to and treat a coronary vessel, coronary valve, or other vascular anatomy. These and other approaches to the repair or replacement of tissue can dislodge particles/debris (emboli) which are freed (released) from the vessel walls and structures causing uncontrolled and unprotected floating emboli to move freely. This freed emboli, and freely floating and uncontrolled emboli can be carried distally (away) via the blood stream and cause issues, such as by blocking or occluding coronary, peripheral, and neurovascular vessels. For instance, during the (TAVR/TAVI) procedure, native tissue can be compressed into the aorta wall to make room for replacement devices. This action may cause dislodging or displacement of arterial plaque, calcium, or thrombus as the devices transverse the aortic arch. These particles can have adverse effects, such as by causing a stroke. These and other matters have presented challenges to a variety of treatment approaches.

Various example embodiments are directed to filter-based apparatuses and their implementation.

According to an example embodiment, an apparatus and/or method involves an extension arm, a frame connected to the extension arm, and a filter having opposing surface areas terminating around a perimeter of the filter. The filter is connected to the frame at the perimeter and configured and arranged with the frame and the extension arm to expand with the frame in a deployed state and, in the deployed state, conform one of the opposing surface areas to an inner sidewall of a tubular organ by engaging the extension arm with respective surfaces of an inner sidewall of the tubular organ and, via the engaging, applying force to the frame that seals the frame and the perimeter of the filter to the inner sidewall. The apparatus can be implemented as part of a catheter, and manipulated to expand while extended from a sheath, and to collapse (e.g., and trap particles in the filter) for retracting into the sheath. Wires or other control mechanisms extending through the sheath can be implemented to control expansion/contraction and conformance of the filter.

Various embodiments are directed to an embolic protection device designed to protect the brain from stroke during left heart procedures, such as those involving TAVR. The functional aspects of dynamic, double-edge sealing of the device are facilitated by control over the system behavior during cardiac output cycle and precise and predictable filtering behavior before and after deployment.

Various embodiments may be implemented with an apparatus that includes a catheter extending from a proximal end to a distal end, a shaft within and operable to move in the catheter, and a filter component that is connected to the shaft and operable to retract within the distal end of the catheter. The filter component includes filter such as a mesh and inner and outer frames connected by struts, with an extension arm connected to the frame. A perimeter of the filter is coupled to the inner frame (and in some instances, to the outer frame), with the inner and outer frame extending along one another. The struts operate to translate a force between the outer frame and the inner frame, applied via the extension arm, such as by applying a force that applies the inner frame and mesh against tissue (e.g., within vascular tissue).

In various implementations, a catheter having a frame, filter and extension arm as characterized herein is inserted into a human aortic arch and the filter component is deployed over at least one artery opening in the aortic arch. Filter material is sealed to a portion of an inner wall of the aortic arch around the at least one artery opening, and used to capture particles in blood flowing into the at least one artery opening. In further implementations, the filter material, frames and struts are collapsed with the captured particles therein, and the mesh, frames, struts and particles are retracted into the catheter which can then be removed.

The above discussion/summary is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in the Appendix filed herewith as well as in the included figures, in which:

FIGS. 3A-3D show respective views of a catheter apparatus, in accordance with one or more example embodiments of the present disclosure;

FIGS. 7A-7G show respective views of a filter support manufacturing apparatus, in accordance with one or more example embodiments of the present disclosure;

FIG. 20 shows pore shape factors that can be used to facilitate pore selection, in accordance with one or more embodiments;

FIG. 21 shows a plot of shape factors, pore diameter and maximum particle size, as may be implemented in accordance with one or more embodiments;

FIG. 27 shows aspects corresponding to respective filter materials, in accordance with one or more embodiments;

FIG. 28 shows a fixture for frame manufacture, in accordance with one or more embodiments;

FIG. 31 shows a manufacturing component for forming a frame, as may be implemented in accordance with one or more embodiments;

FIG. 34 shows a manufacturing fixture for forming an extension arm, as may be implemented in accordance with one or more embodiments; and FIG. 35 shows a manufacturing fixture, as may be implemented in accordance with one or more embodiments.

Figure 1:
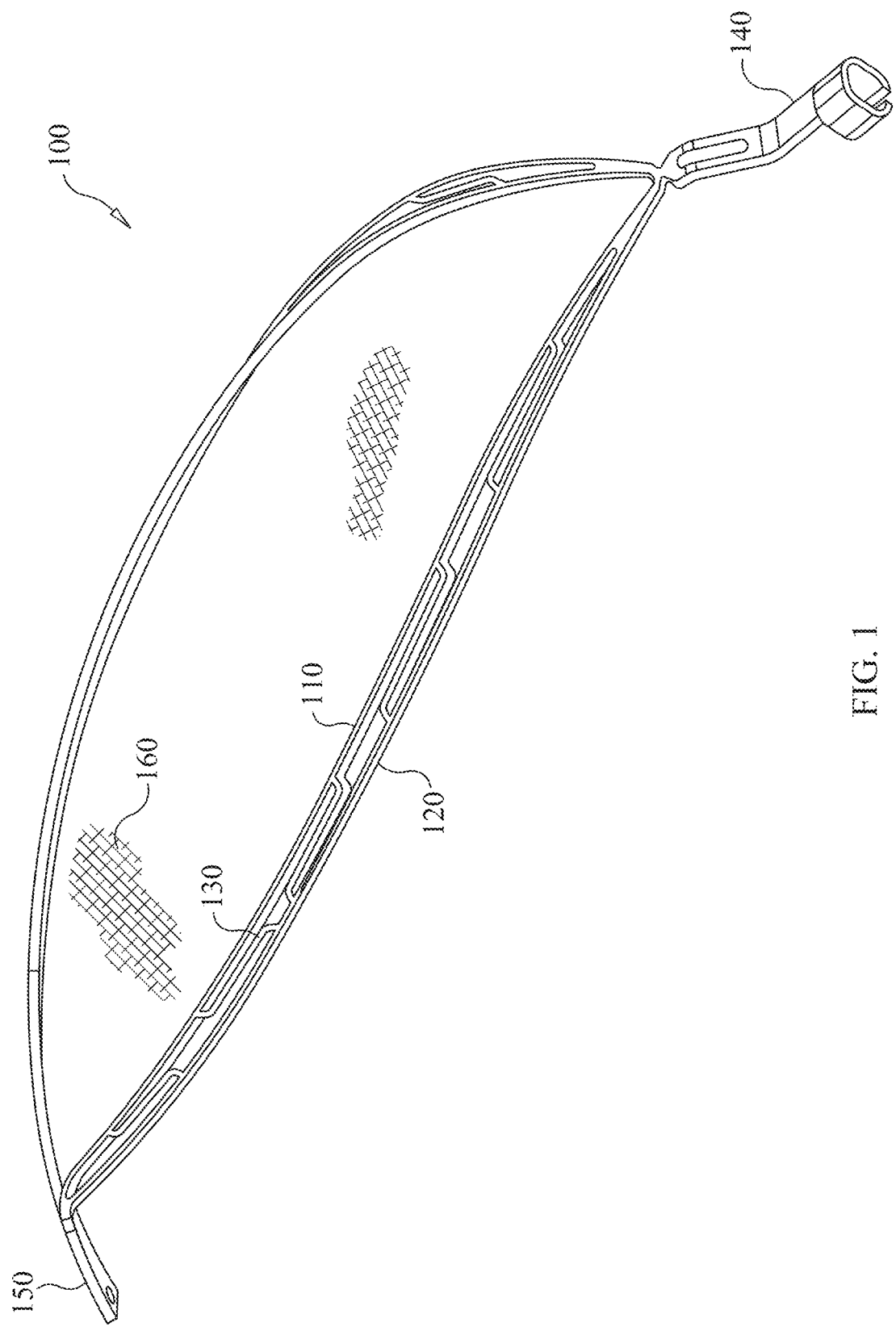
FIG. 1 shows a filter support apparatus, in accordance with one or more example embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving filters, such as may be deployed using catheter-based apparatuses and methods. Various example embodiments are directed to filtering blood flow into vascular tissue, which can be useful for trapping particulates while allowing the flow of blood. In a particular embodiment, an apparatus includes a filter type material that filters particles from blood flow, which is connected to a frame. An extension arm operates to apply a force to the frame, and therein seal the frame and the filter type material to a surface, such as an inner sidewall of a vessel. In the context of these and other embodiments, it has been recognized/discovered that utilizing the frame and extension arm facilitates sealing of the frame and filter to such a sidewall, and that this approach can be particularly useful for conforming and sealing the filter around openings in vascular tissue. This approach can thus be used to mitigate passage of particulates into such openings, which may be particularly useful during surgical procedures. Further, utilizing aspects of stiffness, the filter can be accurately sealed to the sidewall without necessarily obstructing or filtering material flowing within the vessel itself. Such an approach may involve providing a variable compression gasket seal to function as both hemostasis and external fixation ("locking") via compression. The stiffness may be variable across the frame and/or extension arm, to facilitate desired force application and sealing of the filter. While not necessarily so limited, various aspects may be appreciated through a discussion of examples using this context.

Various embodiments are characterized herein, in the figures and in the Appendix (and as may include figures in the Appendix), with specific dimensions, materials and other characteristics as listed. It is noted that such characteristics are exemplary of specific applications, and may be representative of others, with a variety of such aspects contemplated as being implemented accordingly.

In accordance with one or more embodiments, an apparatus includes an extension arm, a frame connected to the extension arm, and a filter having opposing surface areas (e.g., a mesh or other material) terminating around a perimeter of the filter. The filter is connected to the frame at the perimeter and configured and arranged with the frame and the extension arm to expand with the frame in a deployed state and, in the deployed state, conform one of the opposing surface areas to an inner sidewall of a tubular organ by engaging the extension arm with respective surfaces of an inner sidewall of the tubular organ and, via the engaging, applying force to the frame that seals the frame and the perimeter of the filter to the inner sidewall. A shaft may be connected to the extension arm and operable to slide within a catheter, and to position the extension arm, frame and filter relative to the inner sidewall of the tubular organ for applying the force to the frame. The shaft may further operate with the frame to collapse the frame and the filter into a collapsed state, and to withdraw the frame and filter into the catheter in the collapsed state. This can facilitate the capture and removal of particles such as those dislodged during surgical procedures. For instance, with the filter sealed to an opening in a sidewall of an aortic arch, a portion of the filter facing an inner region of the aortic arch may trap particles from blood flowing through the filter and into an artery via the sidewall, and these particles can be removed accordingly.

As noted, a variety of filters can be used. Various implementations involve a filter having opposing surfaces, with a perimeter edge that bounds an outer periphery of the filter. For instance, a mesh or other sheet of material may be used for the filter. Such material may, when laid flat, have a lower and upper surfaces that meet along an edge perimeter of the filter. This edge perimeter can be coupled to a frame and used to seal against the inner sidewall of a vessel.

The frame can be implemented in a variety of manners. In some implementations, the frame includes an inner frame configured and arranged for sealing the filter to an inner sidewall, an outer frame, and a plurality of struts that connect the inner frame to the outer frame. The struts operate to translate force, applied via the extension arm to the outer frame, to the inner frame and therein flexibly conform the inner frame to the inner sidewall. The struts may be operable to facilitate flexure of the inner frame, relative to the outer frame, by providing a spring force and therein facilitate conformance of the outer frame to physical features of the inner sidewall.

The filter may be coupled in a variety of manners. In some implementations, the filter extends within a perimeter of the inner frame and between the inner frame and the outer frame. The struts apply a force between the outer frame and the inner frame and seal an opening in an interior vessel wall by pressing the inner and outer frames against the interior vessel wall and around an opening therein. As discussed herein, the struts may facilitate the sealing under varying pressure conditions such as may result from fluid flow, and with movement of the vessel wall. For instance, the inner and outer frames may be maintained at a displacement distance from one another that varies in accordance with the applied force.

Various embodiments as characterized above and otherwise herein may include some or all of the various described componentry. For instance, some embodiments involve a frame that is operable in accordance with the frames discussed herein. Other embodiments involve a frame and filter coupled to the frame, or the frame and an extension arm coupled to the frame, or the frame, filter and extension arm. Still other embodiments also include a shaft operable to move within a catheter and coupled a frame as noted above. Yet other embodiments also include a catheter extending from a proximal end to a distal end and operable for accepting the shaft, frame and any other componentry. Various functionality, with regard to deployment of the frame, sealing of the frame to an inner sidewall, and retraction of the frame within the catheter, can be integrated among the various components. For instance, with an extension arm having at least two bends along a portion of the extension arm that connects a shaft to a frame, the bends can be used to engage with inner sidewalls and apply pressure to the frame and an accompanying filter. The sidewalls can thus be utilized with spring-like characteristics of the extension arm to facilitate sealing of an opening in the sidewall.

Various aspects are directed to an apparatus for use with a catheter, and including a filter having a frame and an articulated arm connected to the frame. The frame forms a perimeter of the filter and separates opposing surfaces of the filter. The articulated arm is operable to, when deployed within a tubular organ, engage with opposing inner sidewall portions of the tubular organ and utilize the inner sidewall portions to seal filter to the inner sidewall by applying force to the frame.

Various embodiments are directed toward catheter componentry, and providing control over vector-based filter and isolation zone entities to facilitate insertion thereof into a delivery catheter lumen, mitigating potential damage to the catheter componentry, which may involve flush of filter/frame, maintaining an air-free state, packing a vector-based device into a constrained state for transfer into the delivery catheter, and which may be automated. Such approaches may involve a protector component that houses the catheter componentry including the filter and frame. A loader component constrains the catheter componentry in a state that can be controlled and be transferred into the delivery catheter lumen, and is operable with the protector component to provide an air-free environment with a visual indicator characterizing the presence of trapped air within the component. This can provide protection during assembly from rough handling during sterilization and shipping and handling. A handle component facilitates insertion of the catheter componentry from the loader component into the delivery catheter lumen. The handle component may further be operable to lock and unlock to a shaft of the catheter componentry, travel axially over the shaft, and when locked, transfer torque, push and pull forces from an operator through the handle to the shaft and ultimately the filter/frame. Such approaches may be implemented with handle componentry as shown in the figures (e.g., such as shown in FIG. 16).

Some embodiments involve method-based applications with various componentry such as characterized herein, as may involve methods of manufacture and/or methods of using. According to one or more embodiments, a method of manufacturing an apparatus is implemented as follows. An extension arm, frame connected to the extension arm, and filter are provided. The filter has opposing surface areas (e.g., a mesh or other material) terminating around a perimeter of the filter, with the filter being connected to the frame at the perimeter. The filter operates with the frame and the extension arm to expand the filter with the frame in a deployed state. In the deployed state, one of the opposing surface areas is conformed to an inner sidewall of a tubular organ by engaging the extension arm with respective surfaces of an inner sidewall of the tubular organ and, via the engaging, applying force to the frame that seals the frame and the perimeter of the filter to the inner sidewall. In some embodiments, mechanical properties of the frame are optimized by thermo-mechanically processing the frame to set a degree of stiffness that facilitates deployment of the frame and filter within the tubular organ, and sealing of the frame and filter to an inner sidewall of the tubular organ. Thermo-mechanically processing the frame may include setting the degree of stiffness by a combination of one or more of: cold-working of the frame (e.g., Nitinol), applying a shape setting heat treatment temperature, and selecting chemistry of an alloy that the frame is formed of.

One or more use-case embodiments involve using a filter and frame as characterized herein, to filter blood or other flow as follows. The filter is expanded with the frame in a deployed state and, in the deployed state, one of the opposing surface areas is conformed to an inner sidewall of a tubular organ by engaging an extension arm with respective surfaces of an inner sidewall of the tubular organ. Via the engaging, force is applied to the frame and seals the frame and the perimeter of the filter to the inner sidewall. Such operable characteristics may be implemented in accordance with one or more embodiments herein, such as by utilizing an extension arm to engage sidewalls.

Various embodiments are directed to an embolic protection device designed to protect the brain from stroke and embolic debris during left heart procedures, such as TAVR. Dynamic, double-edge sealing of the device is achieved via control of the system stiffness and natural frequency during the cardiac output (CO) cycle. The natural frequency, for implementation in a hemodynamic environment, can be set higher compared to the frequency of the cardiac cycle. Such a higher natural frequency can facilitate lower displacement of the frame and, therein, increased sealing. The device has a frame having a natural frequency (N) that is a function of its maximum displacement (Ds) (at the distal end) relative to an anchoring point (La), articulation of the extension arm and its properties. In various implementations, the stiffness spring characteristics and other aspects of the frame are operable to flex during the CO cycle, such that the frame and coupled filter are maintained in place to seal an opening in the sidewall of an aortic arch. A variety of different filters can be attached to the frame, and used to filter material passing through an opening in a sidewall of the aortic arch. In some implementations, struts are used between respective frame components along with a stiffness of the frame to seal such a filter against the sidewall, and maintain the seal under varying pressure conditions while flexibly moving with the aortic arch. The extension arm may articulate to interact with an inner sidewall of the aortic arch to provide pressure against the frame and flexibly maintain it in place.

Figure 10:
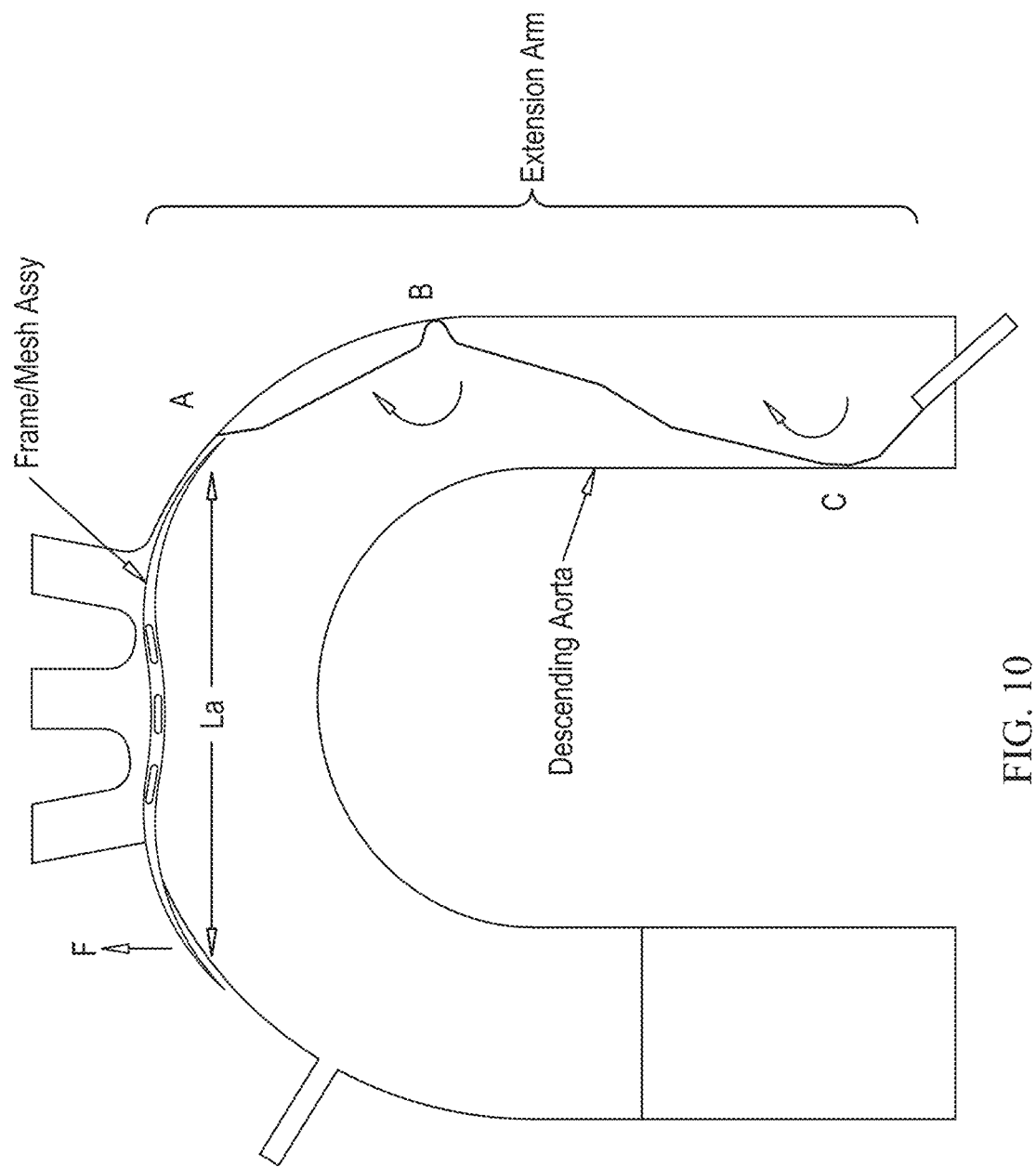
FIG. 10 shows an apparatus deployed within a human aortic arch, with an extension arm applying a force to a filter/frame, in accordance with one or more embodiments.

Turning now to the figures, and referring first to FIG. 10, a frame/filter and extension arm (EA) assembly/system are shown. Anchoring points A, B & C support the EA, creating force (F) and torque (T). The system includes a frame assembly, having a thin filter, wrapped around its perimeter and a supporting extension, at its proximal end. This creates a mechanical force that can overcome hemodynamic forces exerted on the frame/filter assembly. The supporting EA connects the proximal end of the frame assembly. The main functions of the extension arm and shaft are: a) to transfer a push force and torque to push, pull and rotate the frame assembly through the catheter; b) to deploy and position the frame/mesh assembly in the intended location for sealing and filtering; c) to provide the necessary sealing force against the Aortic Arch (AA) wall; d) to provide sufficient stiffness to the frame/filter assembly during cardiac output cycles and arterial pulse; e) to provide various anchoring points along the descending aorta so it can support and reduce frame/filter displacement. FIG. 10 shows the frame/filter assembly and its articulated extension deployed in the AA and descending aorta. The anchoring points: A, B and C support the frame assembly and create the required sealing force (F) and sustaining torque (T) during deployment. A variety of possible combinations may be implemented in Type I, Type, II or Type III arch geometries.

Figure 11:
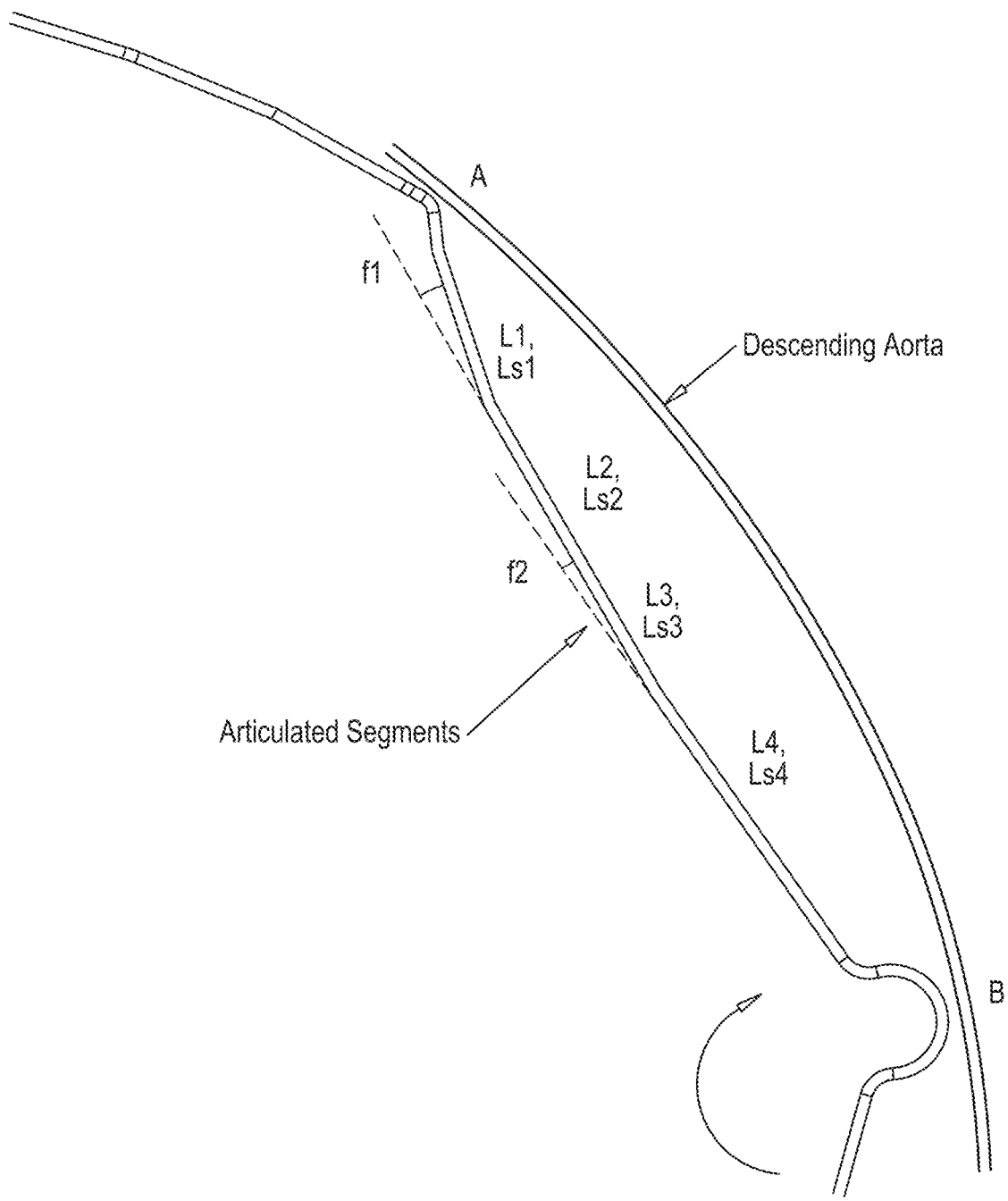
FIG. 11 shows a view of an extension arm, as may be implemented in accordance with one or more embodiments.

Articulation can be implemented in a variety of manners, to suit particular embodiments. In some implementations, the EA anchors at various points (A, B, C, etc.) on the descending aorta and it provides physical support and mechanical spring force for the sealing surfaces of the frame. The EA includes short, angulated segments of specific width, as shown in FIG. 11, that are connected to form a continuous entity. Each segment can articulate and rotate relative to each other, as each contributes to the total stiffness of the EA.

Total spring force (F) and torque (T) of the EA is the sum of all individual force and torque of each articulated section. Articulation of each segment is characterized by segment length (L), segment stiffness (Ks) and segment geometry (width & thickness). The articulating sections of the EA, in conjunction with curved and twisted segments of the EA allow the transition section between the shaft and the proximal end of the frame assembly to maneuver and adapt more precisely to the curvaceous structure of the descending aorta. Total stiffness (K), tip displacement (D), sealing force (F), torque (T), and eventually natural frequency (N) of the frame/filter are controlled by articulation properties of the EA.

Referring again to FIG. 11, articulated segments of the extension arm provide the required sealing F and T to minimize $D_s$. Design parameters of the extension arm that control its properties include: 1) segment lengths (L1, L2, L3, etc.); 2) relative rotation angle ($\Phi1$, $\Phi2$, etc.); 3) segment relative stiffness (Ks); and 4) rotational tendency of each segment as may be clockwise/counterclockwise (CW/CCW) relative to the shaft. Furthermore, physical properties of arm material, linearity and corrosion can affect application. Optimum design may be implemented to ensure that the EA (given the correct combination and sequence of La) would always have a net positive F and T available for sealing the frame/filter assembly against the AA wall.

Figure 12:
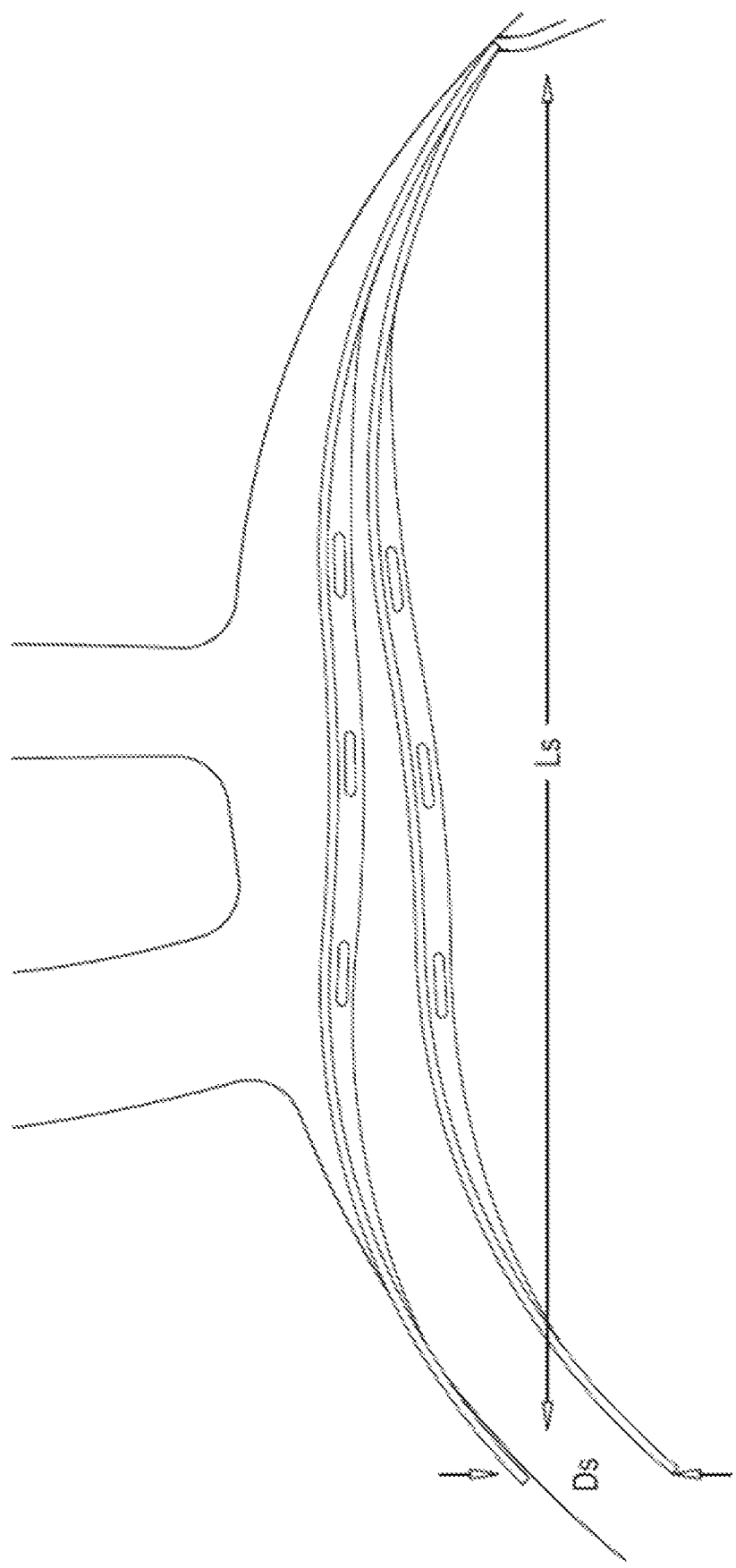
FIG. 12 shows positioning of an apparatus within a human aortic arch, in accordance with one or more embodiments.

Stiffness and natural frequency aspects may be implemented to effect sealing as noted. Main functions include creating a dynamic, double edge seal against the AA wall and filter embolic debris from the three arch vessels' circulation. To achieve this goal, K (ratio of F to Ds) of the articulating EA must overcome the net forces due to Cardiac Output (CO) and the impulsive flow/pressure profiles during each cycle. It is desired for the frame/filter assembly to behave such that when subjected to external forces, it approaches zero Ds without oscillation or separation from AA. Total stiffness (K) of the EA can be set to control how much the frame/filter assembly is displaced from its sealing position. High N of the frame/filter assembly indicates a corresponding high K of the EA (relative to La), and therefore, no or minimal Ds. A lower total stiffness coefficient of the EA, relative to La, indicates a lower frequency, and therefore, a higher Ds, as may be consistent with FIG. 12.

Any separation between the frame/filter assembly and the AA wall is potential for leakage. N of the frame in a CO environment is an indication of how well the K of the EA supports the frame/filter. Stiffness and damping properties of the EA determines how gracefully the frame structure would return to its stable sealing position after being subjected to a sudden CO force or arterial pulse [Eq-1]. For example, fundamental natural frequency of any structure can be crudely approximated by:

$$f_n = \frac{1}{2\pi}\sqrt{\frac{k}{m}} = \frac{1}{2\pi}\sqrt{\frac{g}{\Delta}}, \qquad [\text{Eq-1}]$$

where $f_n$ equals natural frequency in radians per second, K is the stiffness (force/displacement) and m is the balanced mass of the structure. The term under the radical can also be expressed as a ratio of dynamic acceleration to maximum displacement (for purely static displacement) $\Delta$, subject to earth's gravitational (g) acceleration: $f_n=3.13 (1/\Delta) 0.5)$. However, true and actual N and K of the frame/filter structure that is subjected to various hemodynamic forces must be determined experimentally. Position of the La relative to the distal end (Ls) is also an important parameter. As Ls becomes shorter, Ds becomes smaller and the N of the frame/filter and K of the EA increases and the possibility of resonance, and therefore, leakage reduces.

The stability, therefore sealing efficiency, of the frame/filter structure in the AA environment is a direct function of its stiffness and natural frequency. An articulated extension arm as characterized herein allows the frame to anchor itself securely on the descending aorta, pass through a complex geometry and create sufficient sealing force and torque to overcome natural hemodynamic forces of the human cardiac output.

Figure 13:
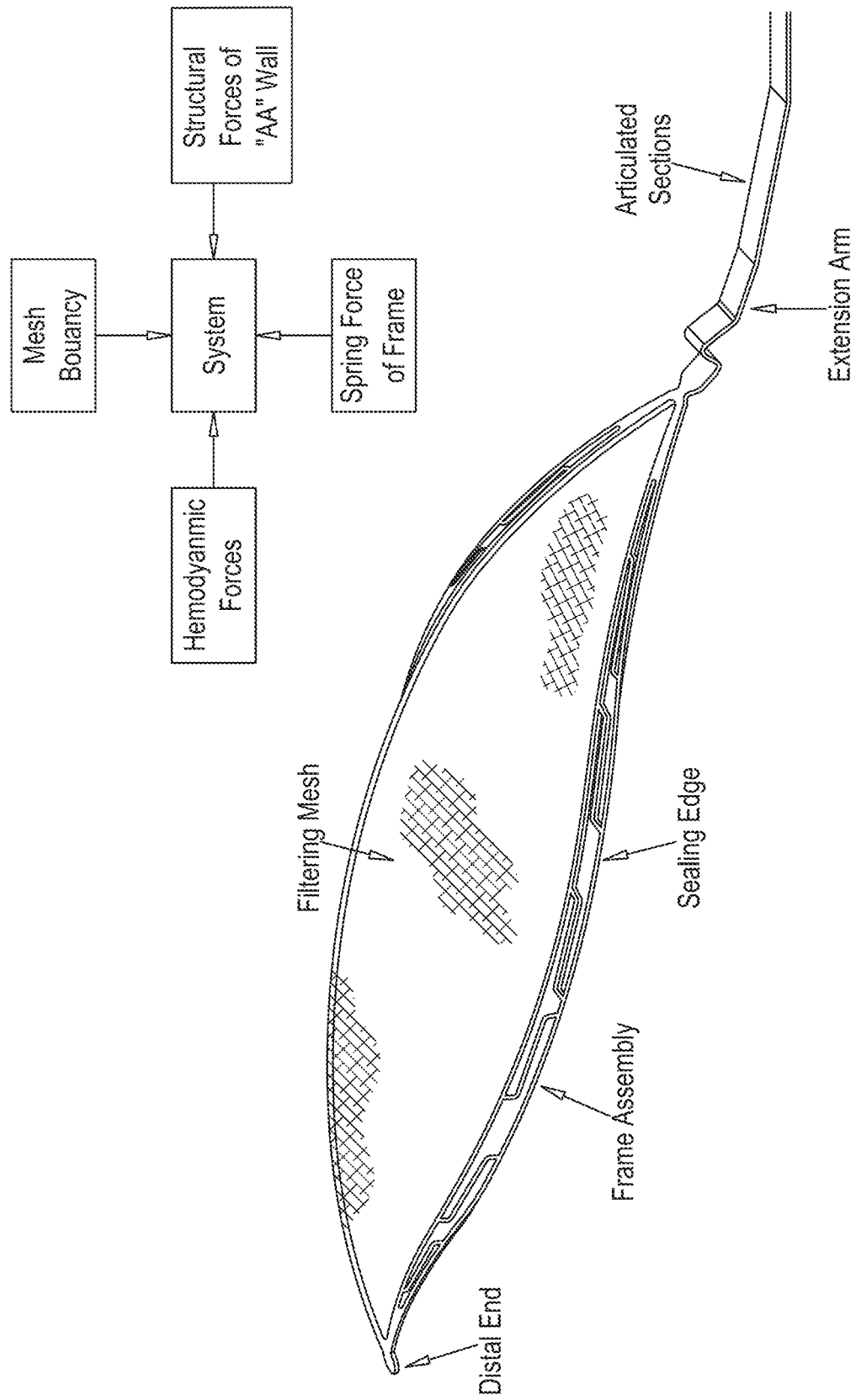
FIG. 13 shows a frame, extension arm and filter componentry, as may be implemented in accordance with one or more embodiments.

Natural frequency (N), stiffness (K) and time constant (Tau) of a frame assembly as implemented herein are utilized to facilitate application in the aortic arch environment of the human body. In various embodiments an embolic device utilizing these aspects is implemented to protect the brain from stroke during left heart procedures focused on TAVR. The functional requirements of dynamic, double-edge sealing of the device demands control over the system time constant as a response to cardiac output cycle. The frame response is directly related to the natural frequency of the structure and its stiffness. The system includes a frame assembly, having a thin film filtering mesh, wrapped around its perimeter and a supporting extension at its proximal end to create mechanical force. In its expanded (or deployed) state, it covers the three main human arteries of the aortic arch, deflecting the incoming embolus. In its collapsed (or packaged) state, it fits completely inside the catheter, prior to deployment. The frame and mesh assembly, when deployed in AA, are subjected to multiple vector forces. They include: a) Hemodynamic forces due to cardiac output (CO), b) Dynamic and structural forces of an oscillating AA wall, c) Buoyancy force of the thin film mesh and d) Mechanical spring forces of frame assembly and its extension that create the sealing force against the wall. FIG. 13 shows an implementation of an apparatus in free space, experiencing main mechanical and hemodynamic vector forces.

Functional aspects may include, for example, those that: 1. Create a Dynamic, Double Edge Sealing against the walls of Aortic Arch, 2. Filter or deflect embolic debris away from the arch vessel circulation, 3. Resist hemodynamic forces of flow, pressure, mesh buoyancy and drag on the filtering mesh film. 4. Conform to anatomic curvature variation of typical Aortic Arch. 5. Minimize the flow of unfiltered blood around the device, 6. Provide adequate area and filtering coverage for the great arch vessels and 7. Provide adequate spring force and stiffness that can reduce system response time during each CO cycle impulse and 8. Prevent system in-phase resonance with CO, having reduced amplification.

The net balance of forces imparted (e.g., frame assembly and the filtering mesh), FNET, during each cardiac cycle, result in adherence and sealing of the system to the superior aspect of AA where the three main arteries arise. The walls of aorta are expanding and contracting radially during each cycle. This oscillation results in the diameter of the arch to increase or decrease accordingly. The frame adapts dynamically to the cardiac cycle such that the sealing of the edges of frame to the walls would remain intact, preventing leakage.

In addition to dynamic edge sealing, mentioned above, adequate coverage around perimeter of the combined arch arteries is ensured such that small displacement of the frame/mesh assembly, due to variation of FNET, over each cardiac cycle output (CO) does not create leakage of blood through the sealing interfaces. Net system vector forces (mechanical and non-mechanical), FNET are configured to push against the sealing interfaces of the frame/AA wall so the filtering mesh can perform its functions without loss of fluid due to leakage.

The pressure-time profile in the Aorta is not a continuously smooth curve; various embodiments address this aspect while maintaining a seal against a sidewall of a vessel such as the aortic arch. Each CO cycle (AP line) produces, three distinct pressure profiles are produced in and aorta, resulting in step-pressure or forcing functions against the frame/mesh assembly. The change in pressure in each zone (DP) results in blood flow rate (Q) in the aorta and flow velocity (V). Flow rate (Liter/Min), can be approximated as Q=VA, where A is the cross-sectional area of aorta at the point of interest.

Figure 14:
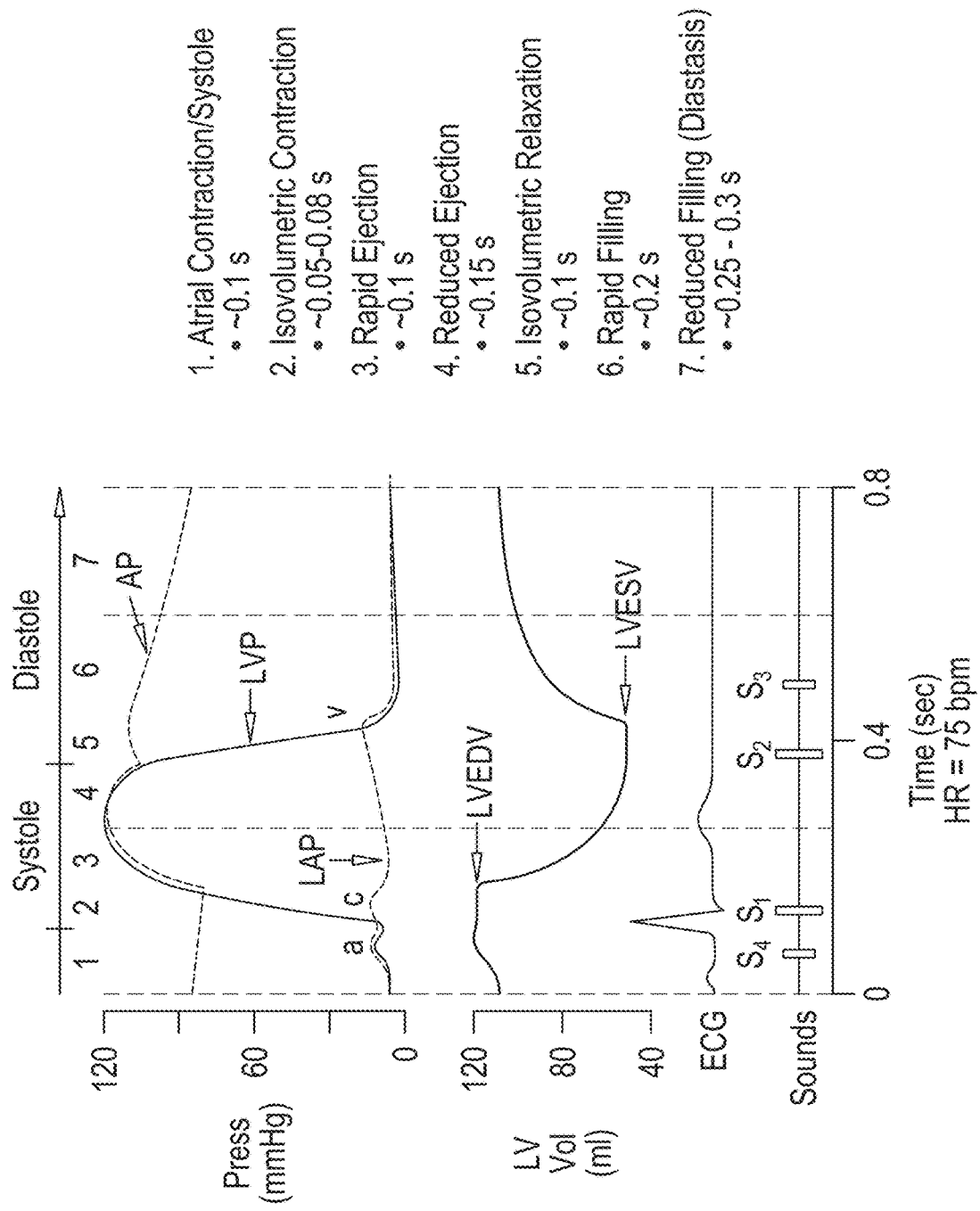
FIG. 14 shows plots of aortic pressure, as may be implemented in connection with one or more embodiments herein.

FIG. 14 shows exemplary aortic pressure (AP) curve where zones "2-3", "3-5" and "5-6" can be identified as having distinct profiles, to which various embodiments are directed at addressing. Pressure step functions, in the Aorta, occur when: a) Aortic valve snaps open and the pressure from LV is pumped into aorta, (appx 0.15 sec; 100 Mm-Hg; Zone "2-4"). b) Aortic valve snaps to a closed state and the pressure in the aorta increases slightly above the value of the pressure in LV due to elastic energy of expanded wall and (Dicrotic Notch—appx. 0.1 sec, zone "4-5") and c) isovolumetric expansion where pressure gradually decreases (appx. 0.2 seconds, 90 Mm-Hg sec., Zone "5-6"). The Dicrotic notch represents the interruption of smooth flow due to brief backflow of blood that closes the aortic semilunar valve when the ventricles relax. Each zone produces a forcing function on the frame assembly. The absolute value of each forcing function is (|FCO|). When |FCO| interacts with the frame/mesh assembly, the net result must be such that |FCO|<FNET without being amplified around its natural frequency. Each step force input can be described mathematically as $$f(t) = \begin{cases} F_0 : t < 0 \\ F_1 : t \geq 0 \end{cases} \quad (1)$$

Figure 15:
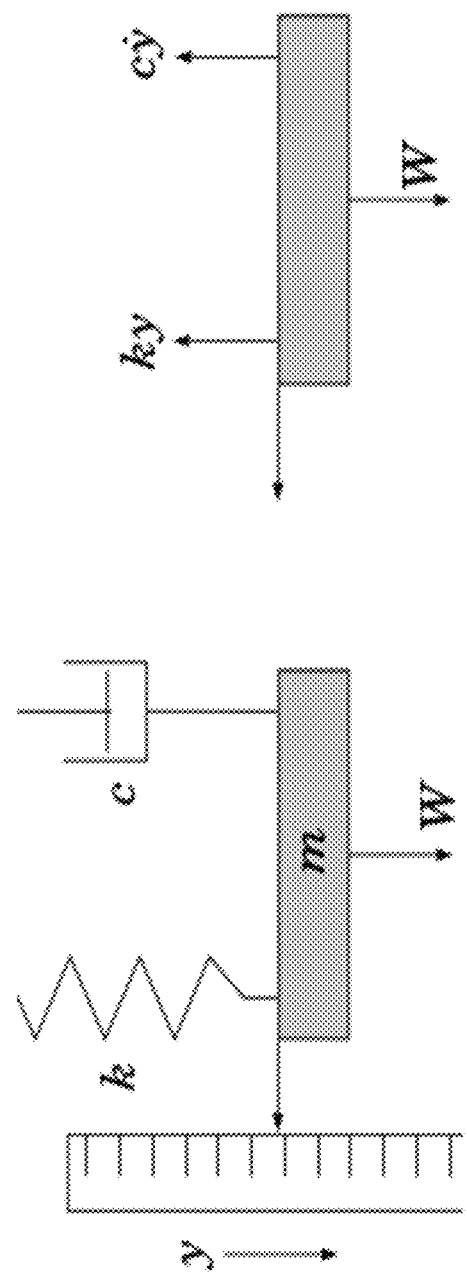
FIG. 15 shows a modeled force application of a frame, in accordance with one or more embodiments.
Figure 16C:
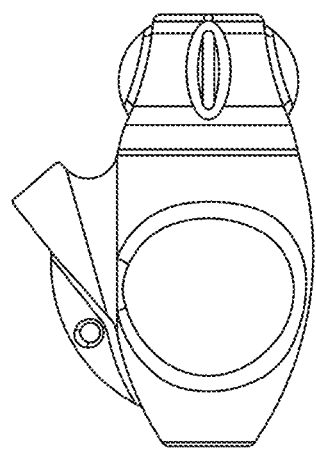
FIGS. 16A-16D show assembly views of a catheter apparatus, in accordance with one or more embodiments.
Figure 16D:
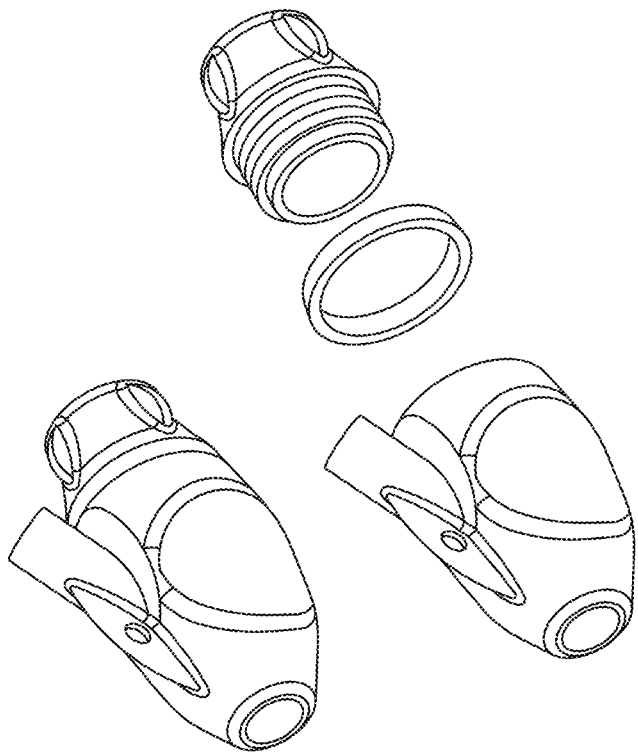
Figure 16A:
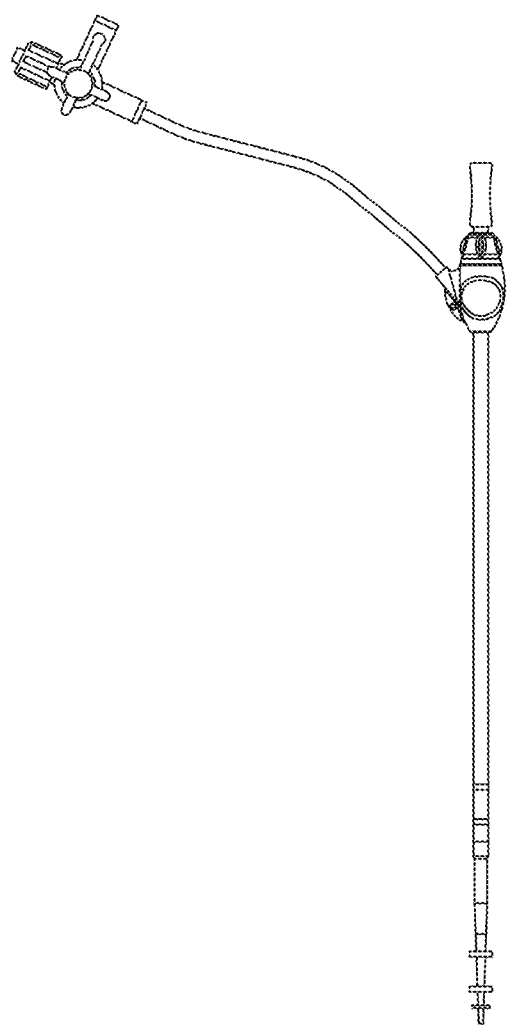
Figure 16B:
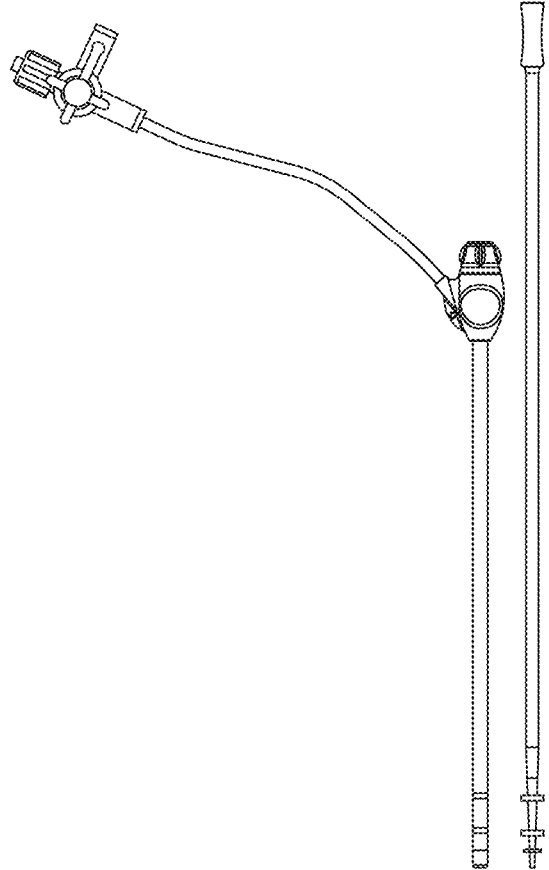

In various embodiments the behavior of the frame/mesh assembly, due to effect of combined forces, FNET, can be expressed as a second order system. The response of the system, the system can be exhibited by exciting to a series of step-pressure (or force) functions in each zone. Step inputs are characterized by fast initial rise time (t) and a flat plateau (F0=0; F1=|FCO|). Second order system behavior can be modelled as a combination of acceleration, mass, damping factor and stiffness parameters. The system reacts to the fast rising input force by either settling within a time constant (Tau) and reduced amplification or no oscillation with higher/lower amplitudes. The behavior (response) of frame/mesh assembly, in the aorta, can be modelled using mass (m), a damping factor (c) and stiffness coefficient (k) as shown in FIG. 15. If the zero value of "Y0" corresponds to the position of the frame (spring) when it is unloaded (immediately after release from catheter), then a force Fs required to move the frame/mesh assembly a distance y is given by Fs=k Y, where k is called the spring constant or stiffness of the system. Parameter "Y" corresponds to displacement of the distal end of the frame assembly. Equation (2) defines the frequency response of the system to a step force input (|FCO|) where "wn" is the undamped (free state) natural frequency of the system and "ζ" is the damping coefficient, related to damping factor (C). In one or more embodiments, a stabilized state is achieved, having no direct or cyclic displacement (change in Y) and within the shortest possible time. The "critically damped" systems (ζ=1) represents the fastest path to point of stability (minimum frame displacement, no cyclic motion and shortest time). These factors alone, however, may be augmented as other design factors may be considered before selecting the correct damping coefficient, natural frequency and ultimately stiffness parameters, for system stability.

It is desired for the system to behave such that when subjected to a step pressure input, it approaches to a zero displacement (Dy=0) fastest and without oscillation. This condition may be called "critically damped" and can be expressed as:

$$\gamma(t) = KF_1[1 - (1 + \omega_n t)e^{-\omega_n t}], \text{ where} \quad (2)$$

$$\omega_n = \sqrt{\frac{k}{m'}},$$

$$\zeta = \frac{c}{2\sqrt{km}}, \text{ and}$$

$$K = \frac{1}{k'}.$$

The main stiffness (K) of the frame/mesh assembly can be implemented by incorporating a series of short-length bent sections in the extension arm (articulated sections). A forced-based system that relies on mechanical spring force, and not hemodynamic fluid forces (such as fluid pressure differential across the mesh) can thus be used to create a sealing force against the aortic wall. The articulated sections have acute angles relative to each other and to the frame. This allows better maneuverability of the frame and simultaneously controls the system stiffness in the desired direction. Directionality and value of stiffness are implemented for balancing functional and mechanical requirements. System stiffness (k) is applied with an appropriate strength and direction to facilitate navigation and conformance to dimensional limitations of a catheter when the frame/mesh assembly is residing inside of it (e.g., packaged-pre-deployment into AA). The length and angularity of the articulated section are tailored to provide a desirable amount of friction inside the catheter, and to facilitate conformance to small radiuses within the AA and its curvaceous and serpentine path as it guides its way through the catheter. A constant sealing force against the cyclically dilating aortic wall are accordingly maintained. The natural frequency is set so that does not amplify and its stiffness, when responding to step-forcing functions, is compliant to a dynamically changing wall. Furthermore, the time to reach to point of stability can be tailored such that it does not overlap into the start of the next forcing function. Time to reach stabilization can thus be set to be less that minimum time step of the forcing function (t).

Stiffness can be set to variably adapt to particular implementations. Functionality can be set by how upper (frame) and lower (extension) parts function and complement each other during operation. Both the frame and the extension part of an assembly have directional stiffness and articulation points on different planes. The frame section includes numbers of rails and braces on either side of its centerline, forming a wider surface area compared to a single round wire. Braces connect the rails together, forming a dynamic spring coefficient that is always in contact with the aortic wall as it expands and contracts due to cardiac cycle. At the same time, this combination of "series" and "parallel" springs (braces) that are imbedded into the frame assembly, can adapt to multitude of degrees of freedom across three-dimensional space. The extension part of the assembly has a unique functionality as well. Its function is to navigate in the lower part of the arch and support the upper portion (frame). It includes various continuous large and small radius bends, having various geometry and material properties (hence stiffness) along its length. By controlling the stiffness of the extension along its curvaceous path and controlling its spatial location, (i.e. targeting the anchoring points to side walls) and twist behavior the natural frequency of the frame, itself, can remain within the design range. The range of the frame's natural frequency can be within 2-15 Hz, however narrower bandwidth can be achieved by controlling the stiffness at different sections of the frame and the extension. The frame and the extension can work as an integrated system, however certain operational independence (isolation) can be implemented to avoid cross-talk between them. Natural frequency and stiffness of the frame are set such that the frame and sealing are not adversely affected (significantly) by disturbances that the extension section experiences due to cardiac output or user input after the frame has been placed at desired location. The function of the articulated section, such as shown in FIG. 13 can be set to "loosely" connect the overall stiffness of the frame and the extension and simultaneously allow a smooth transition between the two so the connectivity remains strong (e.g., like universal coupling of a car axle).

In general, controlling the stiffness any portion of the extension or the frame can be set according to one or more of the following factors: a) Material properties and chemical/physical composition. b) Geometrical stiffness which is a function of shape and size and c) The shape-setting parameters and processes and that can produce a designed material stiffness. The combination and selection of each category can result in continuous and articulated properties of both the frame and extension at each section.

In some implementations, a desired design may be reached by setting characteristics so that the system does not oscillate but approaches its final stable value (y=KF1) slowly and monotonically while at the same time satisfying the functional requirements. The speed at which y approaches its final value depends on the value of ζ. The higher ζ is, the slower value y changes without oscillation. Damping coefficients are set according to a damping factor (c), mass of the frame/filtering mesh and stiffness coefficient. However, the damping factor (c) can be implemented as a variable factor with a value being a factor of mesh density, porosity and buoyancy in a hemodynamic environment. The buoyancy force (in this case) is also a function of volume of blood displaced in the aorta and surface area of the filtering mesh. Hemodynamic drag forces, exerted on the filtering mesh are a function of blood viscosity, mesh surface area and drag coefficient. The smaller the surface area of the mesh, the smaller is the drag force during each step forcing function and it creates less friction inside catheter. Filtering meshes, having higher density than blood, create forces against the spring force of the frame. Lighter meshes can be implemented to reinforce the sealing force against the walls. Equation (3) is a representative of an "over damped" system where ζ>1. The system does not oscillate when subjected to a step input. F1=|FCO| is the initial force due to step forcing function when aortic valve opens.

$$\gamma(t) = KF_1\left[1 - e^{-\zeta\omega_n t}\left(\frac{\zeta}{\sqrt{\zeta^2-1}}\sinh\omega_n\sqrt{\zeta^2-1}t + \cosh\omega_n\sqrt{\zeta^2-1}t\right)\right] \quad (3)$$

Higher values of wn would take the system faster to its final resting point, with coefficient "Tau=ζ wn" being the system time constant. One time constant (1×Tau) is defined as the time it would take for displacement value of the system to reach 62.8% of its final value. Therefore, by controlling and carefully selecting the values of K, ζ and wn the system can be optimized when the effect of friction and buoyancy forces are also considered.

The total time span from zone 2 to zone 6 of AP profile shown in FIG. 14 is about 0.50 seconds. During each CO cycle, the time contribution from each zone of AA is approximately 0.15, 0.10 and 0.25 seconds accordingly. The total system time constant (Tau) must be such that it is always less than shortest rise time of the forcing function in the aorta (<0.10 seconds, here). In addition, an additional safety margin may be set for the system to be completely stabilized before the next forcing function has started. This can avoid oscillation, for example, when FNET is on the same order of magnitude as FCO. (|FCO|=FNET).

Various aspects of the frame and/or extension arm may further be tailored to suit particular needs, such as for loading of the structure within a catheter, reduction of friction inside the tube, expansion of the mesh for greater coverage, negotiation for flexing & bending of the catheter, resistance to push/pull force of the delivery shaft, overcoming buoyance forces of the mesh, when deployed, and overcoming drag forces of the mesh while travelling inside catheter. The frame may be scalable, such that its shape and properties may be kept from one size to the other (i.e. the shape remains the same going from 8 F to 10 F, etc., such as for different implementations). The shape may be achieved by starting flat (e.g., nitinol) material or starting a hypotube followed by laser cut or other methods of cutting. The shape of frame assembly can also have additional features such as additional backbones in the middle or on the sides of the frame assembly. The FA shape may also include various sizes and angulations in both axial and transverse directions to accommodate various aortic arch anatomies and sizes. The frame may be implemented to provide/direct one or more of torsional forces (e.g., resist twist of the AA), vertical forces (push against the coverage area of the three arteries to create a seal), lateral forces (e.g., perpendicular to plane of AA), lateral hemodynamic/fluid forces in cross axis direction, and lateral forces tangent to a plane of AA, and resistance to fluid forces due to cardiac output/hemodynamic forces, and in an axial direction.

With regard to filters as noted herein, a variety of manufacturing approaches and treatments may be employed to achieve desired results. In some implementations, an austenite finish transition temperature above room temperature aiming for Af=32 degree C. is used. Various nitinol shaft properties can be achieved by controlling the cold-work and heat treatment of nitinol wire/rod to achieve a particular austenite finish temperature and therefor desired stiffness and pushability of the shaft.

Shafts as characterized herein can be designed with flexibility characteristics to suit particular needs. For instance, the shaft can be formed to negotiate around tight radius, resist push/pull force/drag forces inside the tube, provide one to one torquability, provide desired stiffness (K value) relative to combined stiffness of the frame & isolation zone, provide reduced superelasticity to achieve optimum stiffness to better negotiate and deliver frame assembly through a tortuous anatomy, create a main vertical force against area of coverage, provide an anchor point for the mesh connection, and torsional force to the frame.

In a particular manufacturing approach, a flat superelastic nitinol sheet with an intended final frame thickness is used, such as in the ranger of 0.008"-0.020". Then, by laser ablation, electro-etching process, or other similar technique the thickness of the nitinol sheet is reduced selectively to approximately 0.001" to create the mesh surface coverage prior to creating the final mesh patterns. Finally, by either laser cutting or electro-chemical processes, the final mesh pattern is created. This provides a one piece nitinol frame assembly prior to the final shape setting. The final shape setting process can be accomplished by proper heat shape setting fixture and heat imparting at about 400° C.-600° C., such as at temperature about 500° C.

The filter assembly can be provided with asynchronous movement (out of phase) relative to CO, which can help eliminate amplification of frame displacement due to CO. Articulation points can be set to provide changes in curvature and stiffness to adapt to a confined geometry across various type of aortic arches. This may facilitate dynamic adaptation/sealing to a variable and changing diameter of the AA. For instance, a CW force can be exerted on AA, post deployment. The articulation may also counter balance the effects of delivery shaft movement (reduce the effect of user movement), and conform closer to the curvature of AA, and to minimize its size and reduce its shape during retrieval inside the catheter.

As noted herein, struts may be implemented to facilitate sealing of a filter to a sidewall as characterized herein. The ratio of cross sectional height to width can be referred to as alpha and used to characterize overall frame stiffness, and directionality of forces created by the frame. For stiff frame applications, an alpha >2 can be used. For medium stiffness, alpha can be between about 1.5 and 2, such as may be applicable where there is moderate cardiac output (CO: 4-5 L/min) and/or the geometry is less confined and the transition area across the arteries are smooth (less sharp turns in AA). Stiffer frames can handle moderate mesh buoyancy forces, thinner/lighter meshes, and friction inside the catheter. For low stiffness, alpha of between about 1.25 and 1.5 can be used, for applications such as those involving low cardiac output (CO: <3.5 L/min) and/or the geometry has a very sharp transition area across the arteries, and for providing low friction inside the catheter and heightened sensitivity to forces caused by mesh in a hemodynamic environment.

Accordingly, combined axial, lateral, and torsional forces of the frame assembly may create an isolated/dampening system so that the frame assembly can be functioned to seal against blood hemodynamic forces (for example, similar to car suspension system). The combination of sealing rails and struts control the lateral and torsional forces. The shape and size of isolation zone controls axial and vertical forces. The natural frequency of the frame assembly can be used as an indicator of how the dampening system functions. The higher the natural frequency of the FA, the better sealing to the arch. Continuously variable stiffness can be used with the FA from the beginning of the isolation zone to the proximal end relative to the stiffness of delivery shaft to provide a more natural cushion during cardiac output and resulting aortic pulsation. It would also provide "PROXIMITY" to the actual curvature of the aortic arch. The stiffness value of FA increases from delivery shaft to the distal end, such that the combined stiffness of the frame assembly is always less than stiffness of the delivery shaft. The combined mechanical forces of FA and hemodynamic mesh of the mesh can be greater than the hemodynamic forces due to the cardiac output and be out of phase relative to frequency of the cardiac output.

Various types of articulation characteristics can be used to promote the FA deployment and better sealing. One involves the mechanical articulation of the FA by itself which can conform better to the more confined and shorter length of the aortic arch. Another is articulation of the isolation zone or extension arm from the proximal end of the frame to the connection to the shaft. The articulation can be provided to better navigate against the curvatures and provide positive clockwise force against the wall of the aortic wall. Yet another involves material stiffness. The combined axial and vertical forces of the frame determine the stiffness of the struts, therefore the resistive force against hemodynamic forces.

Various aspects of frames as characterized herein may be implemented with axial characteristics as follows. The nominal lengthwise radius of the frame accepts shape-constraining forces when deployed in the curved aortic arch anatomy. The aortic arch radius is less than the radius of the frame. This provides a constrained state, via the smaller radius of curvature of the aortic arch, which is used to build potential energy within the frame structure. When the anatomy allows, via arch movement, the potential energy is released to kinetic energy resulting in the frame straightening. This movement works to maintain sealing contact with the anatomy and lengthwise stiffness in the blood flow Various aspects of frames as characterized herein may be implemented with radial characteristics as follows. The specified width of the frame originates from two pivot points, respectively at each end of the frame structure. These pivot points initialize a spreading motion for radial coverage of the filter. The nominal width of the frame is larger than the aorta diameter. When the frame is constrained by the anatomy, potential energy is stored. When the anatomy allows, via aortic dilation, the potential energy is released to kinetic energy resulting in the frame widening up to its nominal state. This movement works to maintain widthwise coverage of the filter and supports sealing contact with the anatomy Various aspects of frames as characterized herein may be implemented with lift characteristics as follows. Shaft, extension arm and frame structures are configured to respectively provide a lift force to the frame, which facilitates interaction with the aortic arch sidewall. The specifications of the componentry are such to utilize the shaft material properties and anatomy dimensions to generate this stored energy. When the anatomy allows, via arch movement, the potential energy is released to kinetic energy resulting in support of the frame structure.

Various aspects of frames as characterized herein may be implemented with pulse characteristics as follows. As an extension of the radial vector, the nominal shape of the frame structure exerts force into the aortic wall for sealing. During the cardiac cycle and related aorta dilation and constriction, the resistance (potential to kinetic) maintains force-based contact with the aorta wall and thus maintain seal throughout dynamic cardiac environment.

A variety of types of filters can be used with various embodiments. Filter meshes may be implemented with behavior, physical and mechanical properties, porosity and chemical and hemodynamic effects as follows. Further, chemical, biological and geometric aspects of a mesh can be combined with general properties of the mesh to suite particular applications. Such a mesh may involve a thin metallic or plastic film wrapped and/or bonded around the perimeter of a frame assembly, such as characterized herein. The mesh may be wrapped around the frame perimeter and a supporting extension, at its proximal end. This creates a mechanical sealing force that can overcome hemodynamic forces exerted on the frame/mesh assembly. The filtering mesh is used to provide a reinforcing and containing structure to the frame assembly and a filtering mechanism that blocks and deflects improper sized emboli particles away from the main arteries. A plastic mesh may be extruded, oriented, expanded, woven or tubular. It can be made from polypropylene, polyethylene, nylon, PVC or PTFE, thermosets or thermoplastics. A metal mesh may be woven, knitted, welded, expanded, photo-chemically etched or electro-formed (screen filter) from steel or other exotic metals for TAVR applications. Thickness of the mesh is also of importance and attributes to its weakness or strength against pull or push force of the frame assembly.

Functions of filtering mesh for TAVR applications include: a) block and deflect unwanted emboli; b) allow minimum flow blockage and resistance to three arteries; c) provide sufficient flexibility inside the catheter (for obtaining minimum volume/collapsed size) and outside the catheter (for allowing and not limiting the frame movements); d) provide sufficient resistance against shear force (tear); e) provide maximum porosity for reducing flow resistance; f) have strong self-bonding strength; g) resist bio fowling while in the blood stream; h) buoyant relative to blood density (so it can augment sealing force of the frame; i) be Stretchable (relative to frame structure, following its dynamic movements in cardiac cycle and inside catheter); j) hydrophobicity; and k) be physically and chemically inert to hemodynamic environment.

Figure 17:
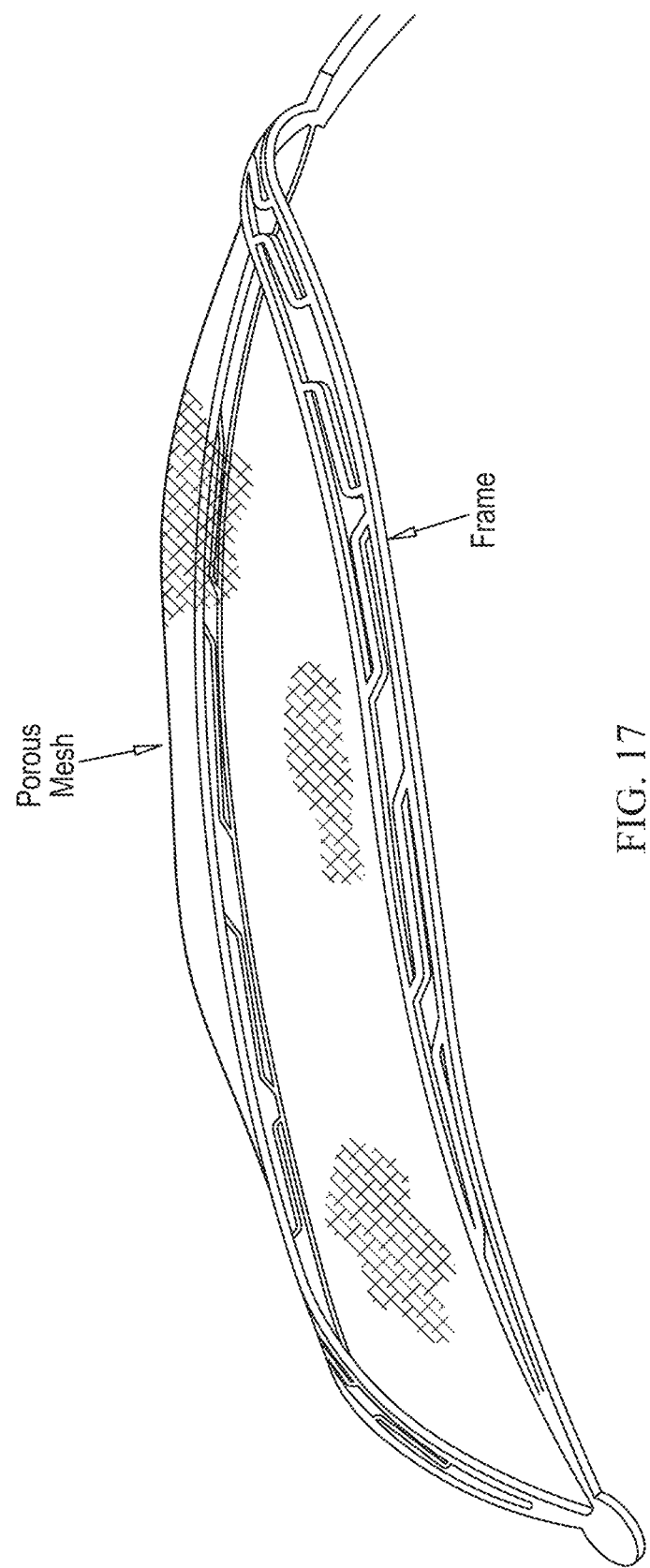
FIG. 17 shows a frame and mesh filter, in accordance with one or more embodiments.

FIG. 17 shows a relevant embodiment, which may be implemented with a frame and porous filter assembly. The mesh film can be ultimately secured to the frame without preventing its dynamic moving and sealing functionality. The flexibility of the frame and mesh assembly will allow sealing to many subsets and combinations that may happen in either type I, type, II or Type III aortic arch geometry.

Figure 18:
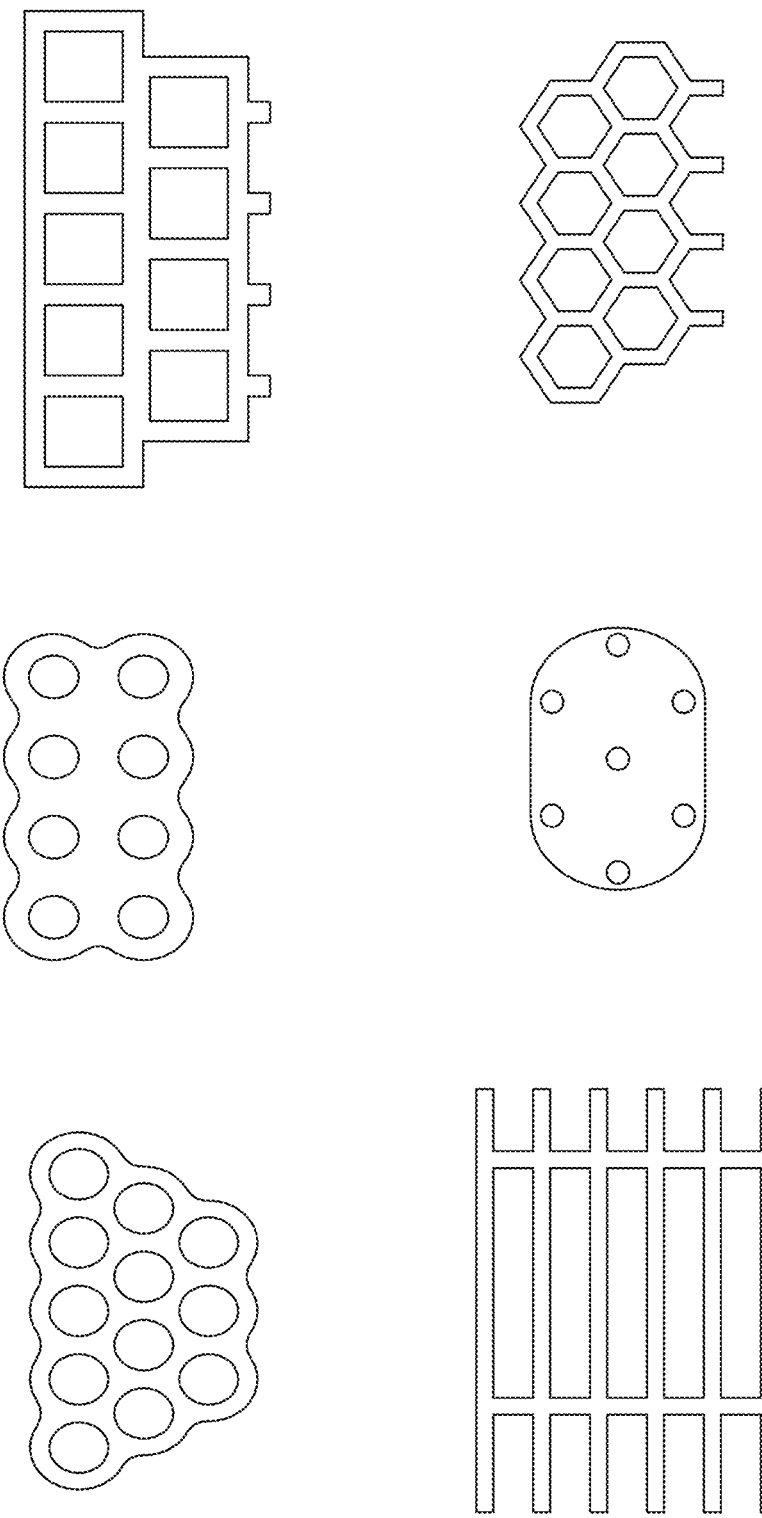
FIG. 18 shows respective filter configurations and related porosity aspects, as may be set in accordance with one or more embodiments.

FIG. 18 shows perforating cell shapes and the percentage of open to total area (% porosity) of films as may be implemented in accordance with one or more embodiments. For example, for the hexagonal cell shape of a perforated thin film, when patterned in a direction, a porosity of 50% or more is achievable. Various implementations provide a maximum porosity available so the resistance to blood flow and velocity can be minimized as the blood enters arteries. As the value of porosity increases, the distance between each cell is reduced and consequently the shear stress that is created, due to stretching or pulling forces, will increase and may eventually result in a tear in the thin film. Shear stress has an inverse relationship to the thickness of the meshed film. The smaller and narrower the spacing between each cell, higher shear stresses will develop in the mesh due to pulling, stretching, folding, in addition to sliding and friction contact against the metallic frame. As such, various implementations utilize films that are set in accordance with these aspects.

A range of particle sizes as may be filtered in accordance with embodiments herein can be differentiated into groups, each of which is defined by their size relative to the membrane pores. One group includes larger particles (too large to fit through any distributed pores or fiber matrices), and another group includes particles small enough to penetrate a membrane's larger pores or fiber interstices, but not its smaller ones. In filtration, a particle's dimensional axis coinciding with the pore functionally are set to suit desired particle size for filtering. Probability factors (e.g., a particle's axial orientations) governed by blood stream velocity, viscosity, and drag can cause more elongated shapes (needle-like) to pass through or lie athwart the pore openings. Thus, in a mixture of particles characterized generally as being too large to permeate a pore or fiber matrix interstice, some shapes may do so depending upon how their flow pattern is directed by either filtration conditions or by chance.

Accordingly, FIG. 18 shows regular geometrical patterns where cell size, pattern and porosity in accordance with filters that may be engineered per functional need of an emboli capturing scheme. Particle size and shape can thus be used to set filter efficiency for particular particle sizes, where an effective filtration area (EFA) is marked by a pore size or retention distribution that is confronted by a particle size distribution. Filter efficiency, h, is related to Beta Ratio, BX, which can be defined as the number of particles before (NIN) and after NOUT filtration, related to a specific particle size (x):

$$BX = BIN/BOUT$$

Accordingly, the filter efficiency, h (%), is related to Beta ratio (BX) as:

$$\eta(\%) = 100 - (100/BX)$$

As BX increases, the efficacy will increase accordingly. For example, for BX=200, h=99.50% and for BX=1000, h=99.90%. The distribution density function determines the average and peak number of particles (BX). The probability distribution function (PDF) for a property defines quantitatively how the values of that property are distributed among the particles in the entire population. Several empirical distribution functions can be implemented to represent the size distribution of many particle populations quite accurately in practice and these are useful in several embodiments. Example functions that are implemented in accordance with one or more embodiments include:

a. Rosin-Rammler distribution function defined by $$P(D) = 1 - \exp[-(D/D_{63.2})^\alpha],$$

where D=63.2 is the size at which the distribution function has the value 0.632.

b. Log-Normal distribution defined by:

$$P(D) = G\left(\frac{\ln(D/D_{50})}{\sigma}\right),$$

where G(x) is, the function defined as:

$$G(x) = \frac{1}{\sqrt{2\pi}} \int_{-\infty}^{x} e^{-t^2/2} dt,$$

$$\sigma = 1/2(\ln D_{84} - \ln D_{16})$$

which is called the Gaussian or Normal distribution function. It is tabulated in many mathematical and statistical reference books and it is easy to obtain values for this function. In this distribution D50 is the particle size at which P D50=0.5. It is called the median size.

c. Logistic distribution defined by:

$$P(D) = \frac{1}{1 + \left(\frac{D}{D_{50}}\right)^{-\lambda}}$$

These three distributions are two-parameter functions and they can be fitted closely to measured size and how they are distributed by curve fitting techniques. Therefore, by determining the distribution of the particles for their respective properties (size, shape, mass, velocity, etc.), the most probable particle distribution can be determined for estimating filter efficiency, and utilized as such to set characteristics for various embodiments.

Figure 19:
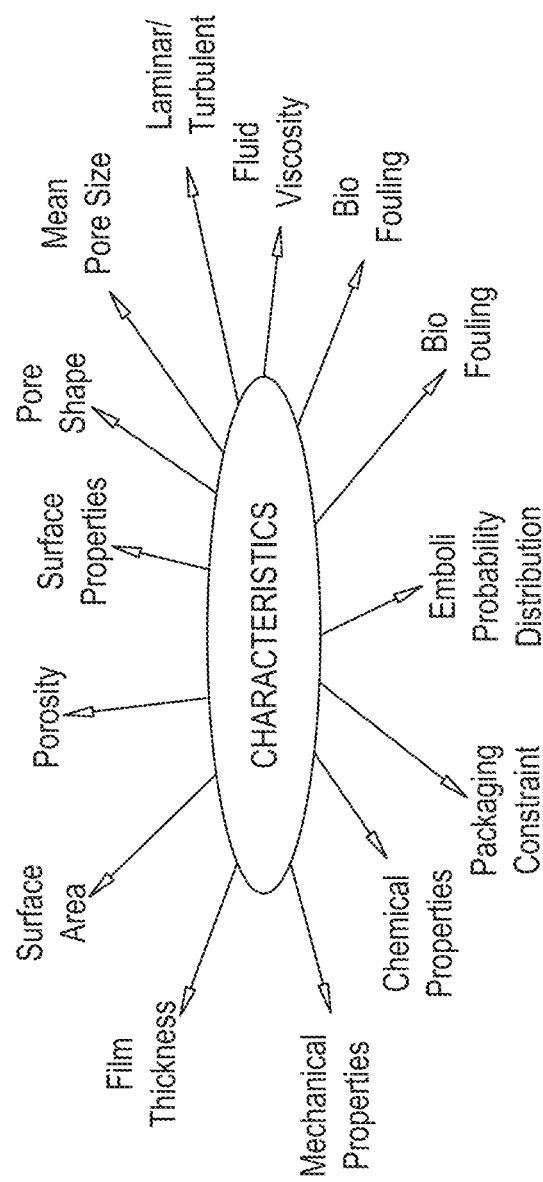
FIG. 19 shows a plot of factors that can be used to facilitate pore selection, in accordance with one or more embodiments.

FIG. 19 depicts factors that are considered in setting pore size, in accordance with one or more embodiments. Pore structure of a textile or plastic thin material can be varied depending upon the application of film. Pore cross section may be elliptical with minor axis, d, and major axis, n*d. By assigning different numbers to the axial ratio, n, a variety of pore cross-sections may be represented. For a pore having elliptical cross-section, measured pore diameter is D, can be estimated as:

$$D = 4d/[8(1+n^2)/n^2]^{1/2}.$$

For example, for pore size of 125 microns and for n=1, 1.5 and 2, the particle sizes that may not pass through are 125, 147 and 158 microns accordingly. The largest particle that can pass through the elliptical pore is d. The ratio of the diameter, d, of the largest particle that can pass through and the measured pore diameter, D, is the pore shape factor, it is given by:

$$\lambda = [d/D] = [(1+n^2)/2n^2]^{1/2}.$$

FIG. 20 shows pore shape factors approximating various cell shapes as may be implemented in accordance with one or more embodiments. FIG. 21 shows a comparison of the maximum diameter of particle that can pass through pores obtained from a fiber diameter and mesh count of fabric and from the pore diameter measured by a porometer. Mesh performance inside a catheter and its reaction to friction and dynamic loading can be resolved prior to deployment of frame and mesh assembly in aortic arch. In accordance with one or more experimental-type embodiments, average sizes of openings in polyamide fabrics computed from fiber diameters and mesh counts are in good agreement with the largest particle that can pass through computed from the pore diameters measured by a porometer. Measured pore diameters may be made comparable with d by including a multiplying factor.

Mechanical properties of a film (or woven/non-woven material) can be used to determine a first aspect of the filter properties. These properties include, yield stress, strength (area under stress/strain curve), strain, modulus of resilience (modulus of resilience=(yield stress)$^2$ over 2*Young's modulus), toughness (energy of mechanical deformation over volume) and Density. Properties related to the perforated film or woven fabric may include: stretchability, flexibility and tear resistance. Film properties related to one or both of physical and geometrical (mesh related) can be set to suit particular applications.

Stretchability of a perforated film (s) or fabric can be defined as combined percentage of elongation of the film, direction, relative to its original length (e), before it exceeds a linear stress limit of the material. Reaching such a stress limit can result in shear stress and tear near cell sites, plus maximum shape change ($\beta$) of the meshed cell due to stretch. (s=$\epsilon$+$\beta$). Material strain, ($\epsilon$), is defined as the ratios of displacements divided by reference length and it is related to intrinsic property of the film material. The shape change, $\beta$, is related to the geometry of the mesh and how much is elongated/stretched relative to original pore size ($\beta$=1−L0/LS) before reaching the maximum stress that creates a tear in the material near cell sites. Various embodiments are directed to mitigating shear and tear, accordingly.

Figure 22:
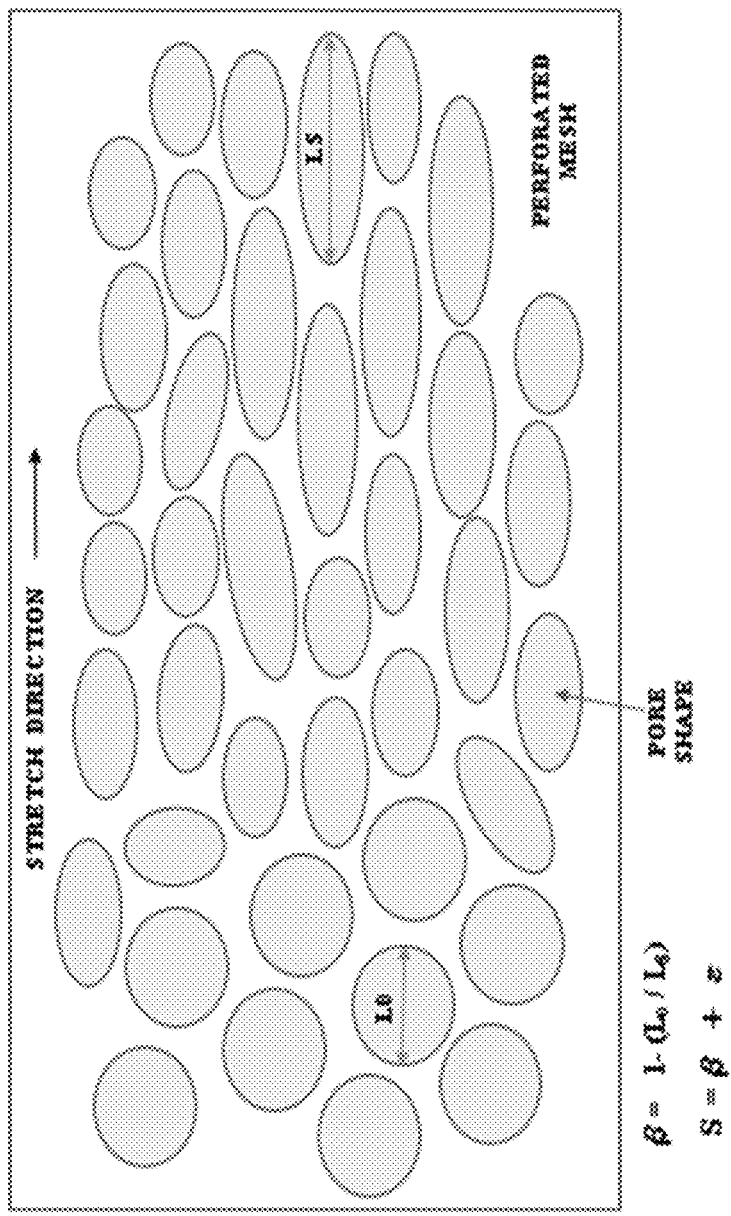
FIG. 22 shows pore stretch characteristics, as may be implemented in accordance with one or more embodiments.

FIG. 22 shows pore stretch characteristics, as may be implemented in accordance with one or more embodiments. The tear can occur either due to $\beta$ or $\epsilon$ depending amount of stretch or value of strain. For thicker films, having higher values of yield, ultimate strength, toughness and low porosity (below 25%), the possibility of shear stress and tear occurrence due to material strain is high (polyester mesh with low porosity). On the contrary, if the mechanical properties of the material are lower but the porosity remains the same, having the same thickness then the cell tear can occur due to cell shape deformation and stretch ($\beta$). Accordingly, filter designs are implemented accordingly to address potential issues in this regard.

The flexibility of filters as implemented with embodiments herein can be set to suit particular applications. The flexibility of perforated thin film is the ability of a material to deform elastically and return to its original shape when the applied force is either removed or reversed. The film adapts to external changes (folding, bending, twisting) elastically. The more flexible an object is, the less stiff it would be. Flexibility of a perforated thin film will cause a very small strain in the material ($\epsilon$=0) during shape changing (where internal stresses in the film are negligible). This can be attributed to shape changing of the film and its ability to flex and navigate within many degrees of freedom. Flexibility can be quantified, quite mechanically, as the inverse of stiffness (1/k) where k=force/deformation. However, for thin flexible and perforated films other factors can be included. Thermoplastic or thermoset thin films, for example, will fold under their own weight. If held on one side, a perforated thin film will fold and bend and change shape due to force of gravity. It can be twisted many times, while held at one end, before stretch and stresses take over causing shear stress and tear. Therefore, the definition of foldability (NF), bendability (NB) and twistability can be incorporated to define how flexible a perforated thin film can be. It is also apparent that as the percentage of porosity increases, the thin film will be able to adapt to more external changes (adapt to more degrees of freedom). Specific gravity of the film material is also a factor in fluid buoyancy or gravitational environment. Bendability (NB=r/t) is defined as the ratio of minimum bend radius (r) to film thickness (t) without causing tear or permanent deformation in the film. Foldability (NF) is defined as the maximum number of times a strip length (L) of a thin film can be folded in half, in the same direction. For a single direction folding, the exact required strip length (L) is $$L = \frac{\pi t}{6}(2^n + 4)(2^n - 1),$$

where "t" represents the thickness of the material to be folded, "L" is the length of the film to be folded in only one direction, and n represents the number of folds desired.

An upper bound and a close approximation of the actual paper width needed for alternate-direction folding is $$W = \pi c t 2^{(3/2)(n-1)},$$

where W is the width of a square piece of paper with a thickness of t, and n is the desired number of folds to be carried out in alternate directions. Above equations give an approximate value of $N_F$ for a width and length of a thin material. The actual value, however can be determined experimentally.

Twistability (NT) is the maximum number of time a strip of thin film can be twisted in the same direction before causing stretch or stress in the film. One twist is equivalent to 360 degrees of rotation around axis of symmetry of the film. During twisting, film's initial length will decrease as the number of twists increases until the film cannot be twisted any more without the entire twisted article start to bends over itself. To summarize, Flexibility (FL) of perforated thin mesh can be defined as the product of the factors, mentioned above, where 6 and rare porosity and specific gravity of the thin film accordingly, as follows:

$$FL = 6 *r*NF*NB*NT$$

Tear resistance is the ability of the material to resist shear stress. Thermoset materials may have higher yield stress and modulus of elasticity, and therefore their resistance to tear can be higher compared to thermoplastic materials. In analyzing the maximum shear stress of the material due to external forces, the stress intensity factor (KF) due to shape of the pore can be considered. A circularly shaped pore has less stress intensity factor compared to a hexagonal one. A hexagonal shaped pore, having six vertices, is more susceptible to high stress during shape changing (e.g., bending, flexing, and stretching) than a circular one. Tear force (F) can be can be estimated as:

$$F = (1/KF)*S*t*L$$

where s=shear strength of the film, t=thickness, L=length of the film and KF=stress intensity factor (that can be determined analytically or experimentally).

Biodegradation characteristics of filter material can be set to address certain embodiments and implementations. Biodegradation in a biological environment may be defined as a gradual breakdown of a material mediated by a specific biological activity. Oxidation, hydrolytic, and enzymatic mechanisms can occur with biodegradation. When materials are exposed to body fluids, they may undergo changes in their physicochemical properties because of chemical, physical, mechanical, and biological interactions between the material and the surrounding environment. Biodegradation processes could be driven by chemical, physical, and biological interactions. Biodegradation rate within an organism is related to filter (e.g., polymer) characteristics and the place in the body where the filter will be exposed. Chemical degradation is influenced by composition and molecular structure, polydispersity, crystallinity, surface area, hydrophilic or hydrophobic characteristics. In general, chemical degradation causes the deterioration of the main polymer chains by random cleavage of covalent bounds, depolymerization or crosslinking of linear polymers, interfering with a regularly ordered chain and with crystallinity, decreasing certain mechanical properties. Degradation can be by surface degradation or bulk degradation. In the case of bulk degradation, water uptake by hydrophilic polymers is faster than the rate of conversion of polymer into water-soluble materials, bulk degradation causes the collapse of all the material since the degradation process occurs in throughout their volume. Surface degradation appears in hydrophobic polymers, leaving the inner structure intact, these polymers offers a better control of degradation rates. Biodegradation characteristics can be set to facilitate interaction with the immune system and their specialized cells.

Figure 23:
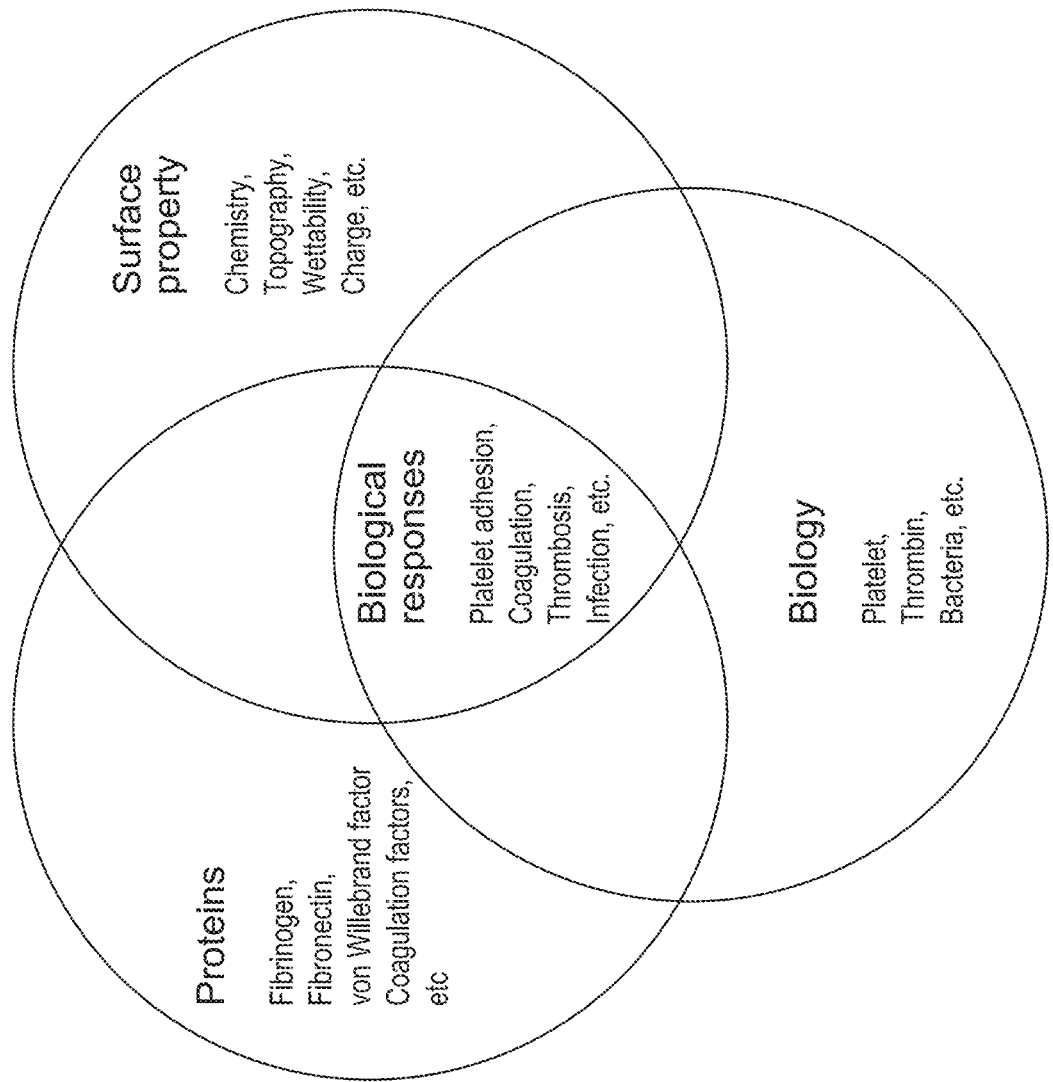
FIG. 23 shows filter biological response characteristics, as may be implemented in accordance with one or more embodiments.

FIG. 23 shows biological responses of material, which can be considered in connection with the selection and implementation of filter materials. Hemocompatibility of a biomaterial can be set to facilitate the overall success of biomaterial in the body. Implanted biomaterial can cause an immune response by the host tissue. A film's mechanical and physical properties can thus be set to that it is inert in the presence of blood PH and viscosity. Polymeric materials as may be implemented for various embodiments can generally classified into three different classes depending on their source: natural polymers, obtained from natural sources including both plant and animal origin; synthetic polymers, based on totally synthetic sources; and bio-inspired polymers which include materials synthesized to mimic a naturally occurring polymer, but not necessarily identical to it. Blood—material interactions can trigger a complex series of events including protein adsorption, platelet adhesion and activation, coagulation, and thrombosis. For example, platelet adhesion and activation on biomaterial surfaces is influenced by surface properties such as energy, charge, and composition. The intensity of response depends on many factors, including the properties of the material itself. Hemodynamic response to the biomaterial follows different pathways. Coagulation, thrombin formation and platelet adhesion rapidly follows protein absorption by the film. This is influenced by the amount of fibrinogen adsorption, which can occur spontaneously on biomaterials as with platelets, leukocyte adhesion is influenced by the layer of adsorbed proteins, but they are also recruited by the signals released by activated platelets and injured cells.

Figure 24:
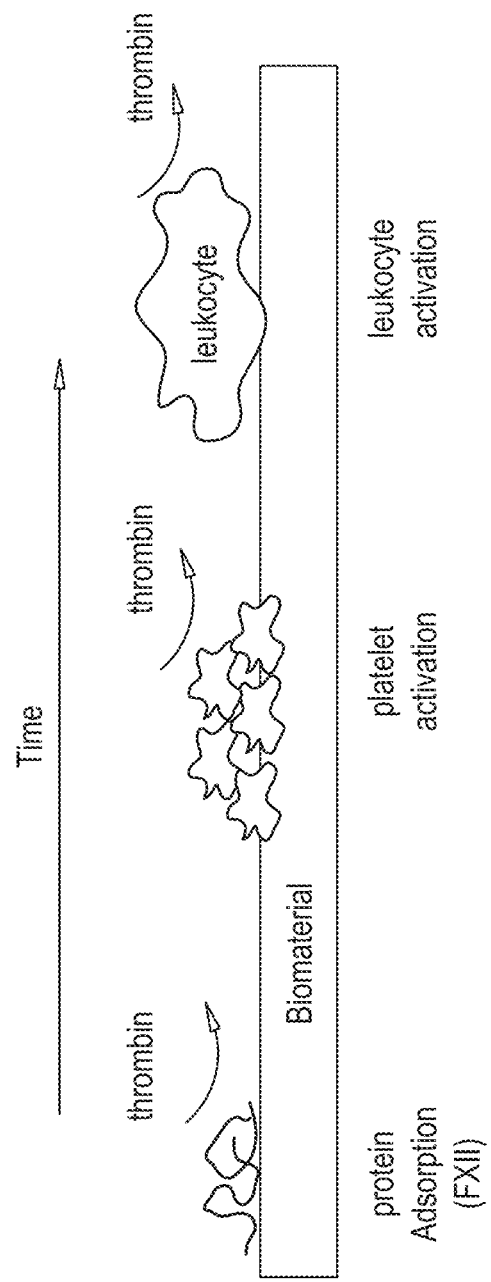
FIG. 24 shows biomaterial response, as may be implemented with a filter in accordance with one or more embodiments.
Figure 25:
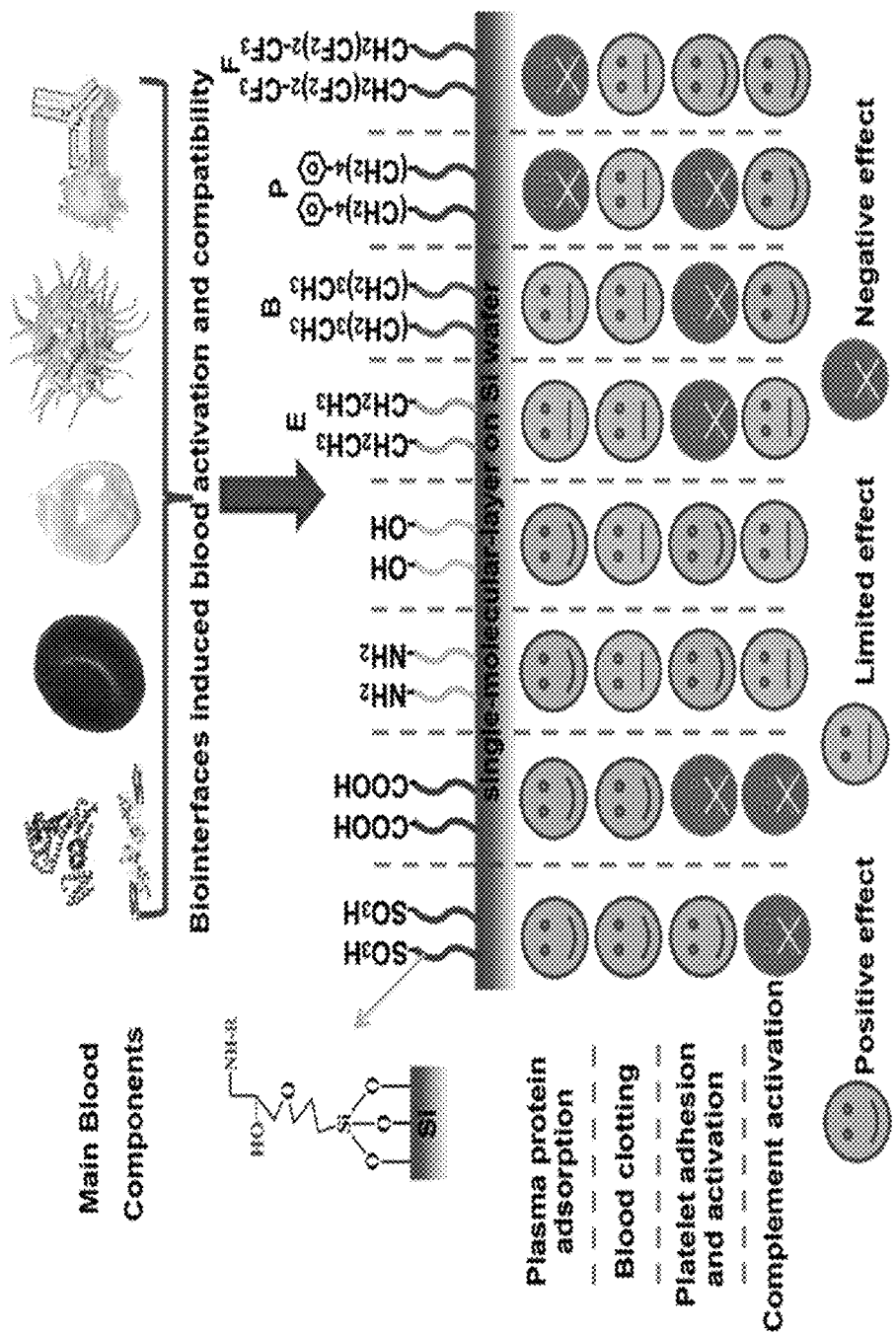
FIG. 25 shows surface activation effects as may be implemented with a filter material, in accordance with one or more embodiments.

FIG. 24 shows an approximate time scale of protein adsorption, platelet adhesion and leukocyte adhesion during an immune response to an implanted biomaterial, which can be used to set material characteristics, in accordance with one or more embodiments. FIG. 25 shows surface compatibility of a single molecular layer deposition of various activators on the surface of a polymer, and effects of various surface activation on hemocompatibility of a polymer, as can be considered in the design of filters for various implementations. The two different pathways of coagulations (complement & platelets) are not independent of each other. When coagulation is induced by the extrinsic pathway, the intrinsic pathway will still contribute to thrombin formation, playing a significant role in propagation of the response. Leukocytes and platelets co-stimulate each other. Activated leukocytes promote increased platelet aggregation, which in turn increases leukocyte activation. Thus, adhesion and activation of leukocytes affects platelet adhesion and activation, which in turn affects the coagulation cascade. With biomaterials, however, this reaction elicits degradation of the material and a prolonged inflammatory response. Therefore, Polymeric films can be activated (either surface or bulk) against coagulation and creation of blood sludge on the surface or blocking the pores of filtering mesh. Wettability of the surface and its affinity to attract and attach blood particles to itself, is another aspect of compatibility that can be considered with filter design. Surface functionalization can thus be chosen to allow the capture or continuous bombardment of the porous medium by the emboli but mitigate or prevent biodegrading.

Approaches for the modification of polymeric membranes with improved blood compatibility include: a. bulk modification of polymeric material, and then to prepare modified membrane; b. surface modification of prepared membrane; and c. blending, which can also be regarded as a surface modification. An in situ cross-linked polymerization can be used for the modification of a PES membrane using different monomers of AA, VP, and NaSS with the same weight ratios.

Figure 26:
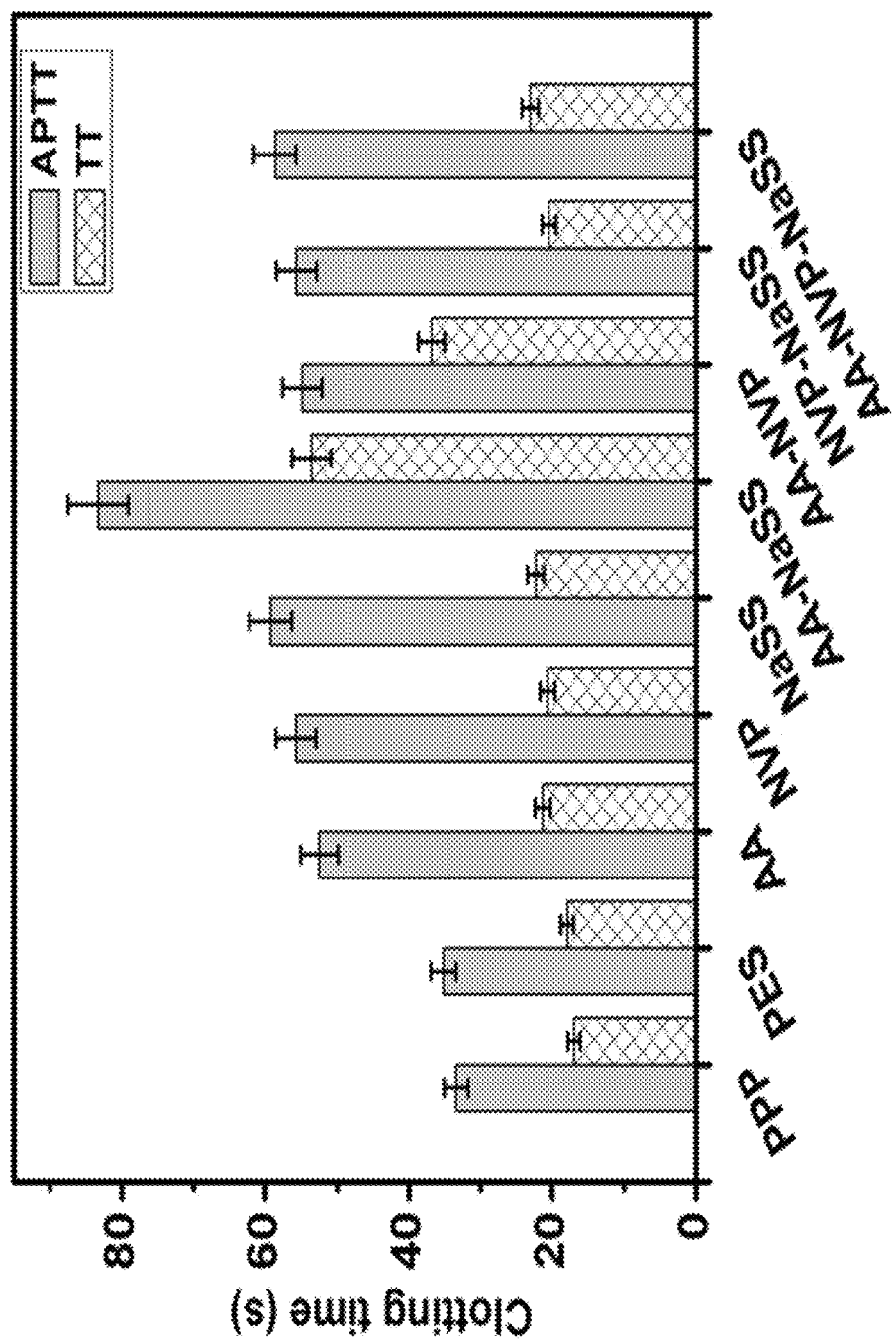
FIG. 26 shows clotting times for materials, as may be implemented in accordance with one or more embodiments.

FIG. 26 shows clotting times for materials, as may be implemented in accordance with one or more embodiments. An anticoagulant property of membranes can be thus evaluated by activated partial thromboplastin time (APTT) and thrombin time (TT). Activated partial thromboplastin times (APTTs) and thrombin times (TTs) for the membranes modified by PAA, PNVP, NaSS and the copolymers are shown.

FIG. 27 shows comparison between mechanical properties of selected polymers as may be implemented in accordance with one or more embodiments. Exemplary properties include resistance to tear, higher ultimate strength, elongation prior to breakage and modulus of elasticity. In addition to above mentioned properties, bulk, surface and geometrically dependent properties are important for application involving emboli protections devices. These additional properties include resistance to biofouling, bio compatibility, flexibility, foldability and ability of material to bond to itself without assistance of secondary liners. The last category can facilitate the assembly of the polymer to anchor itself to the frame structure without creating additional bond and joint volume.

A variety of approaches and apparatuses can be implemented for manufacture and implementation of a filter assembly as characterized herein. FIG. 28 shows a fixture for frame manufacture, as may be implemented in accordance with one or more embodiments. The fixture includes respective portions corresponding to a frame and extension arm for geometry that may facilitate application of the filter for conformance to a sidewall of a tubular organ, such as the aortic arch.

Figure 29:
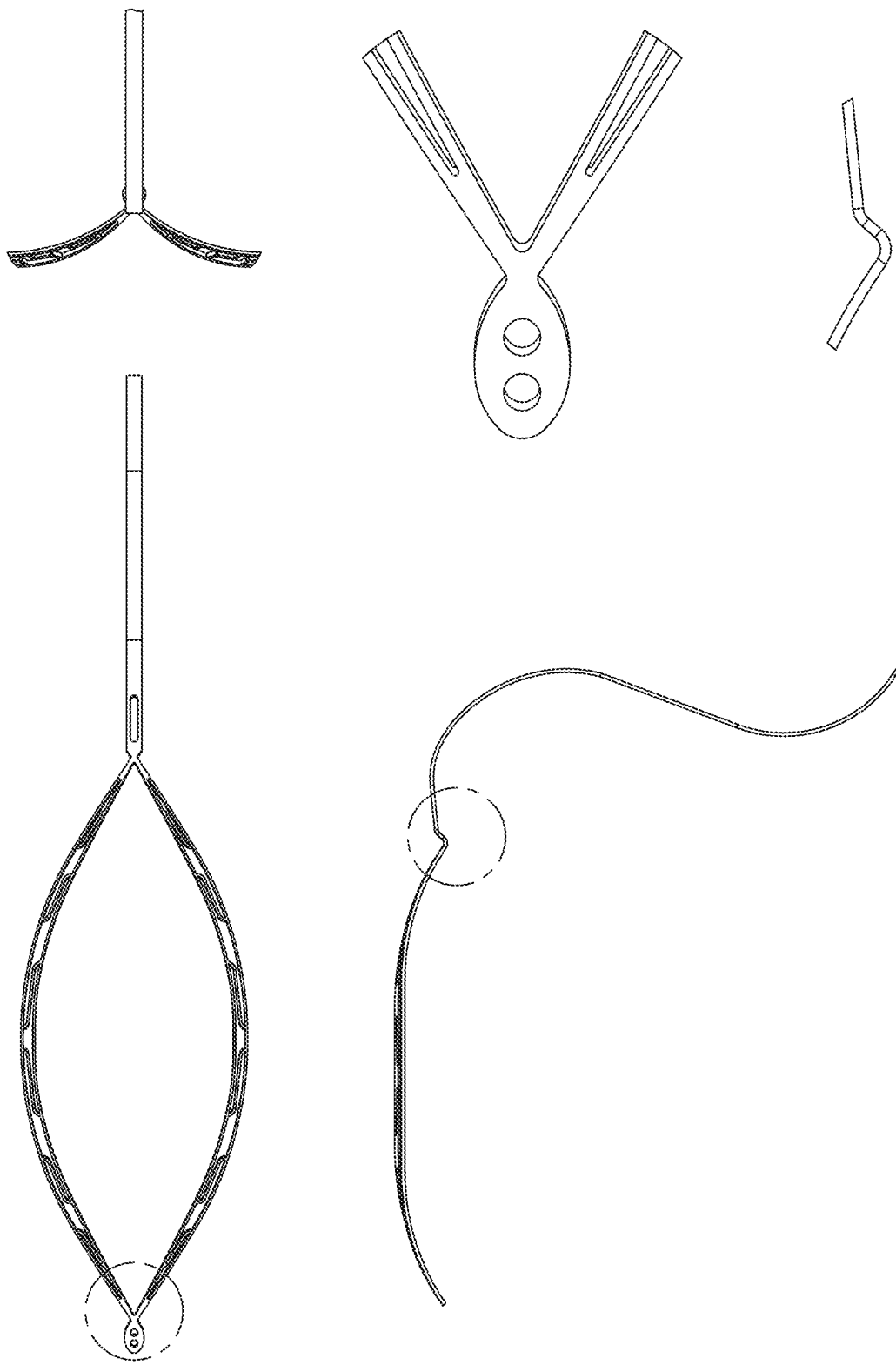
FIG. 29 shows an apparatus including a frame and extension arm, as may be implemented in accordance with one or more embodiments.

FIG. 29 shows an apparatus including a frame and extension arm, as may be implemented in accordance with one or more embodiments. The apparatus in FIG. 29 may be manufactured, for example, utilizing the apparatus as shown in FIG. 28. A top view in the upper left shows filter portions (inner/outer) with struts between. A side view at the lower left shows the frame and extension arm, as may be inserted within an aortic arch such that the bends in the extension arm interact with sidewalls therein. Detailed cross sections are shown at the lower left.

Figure 30:
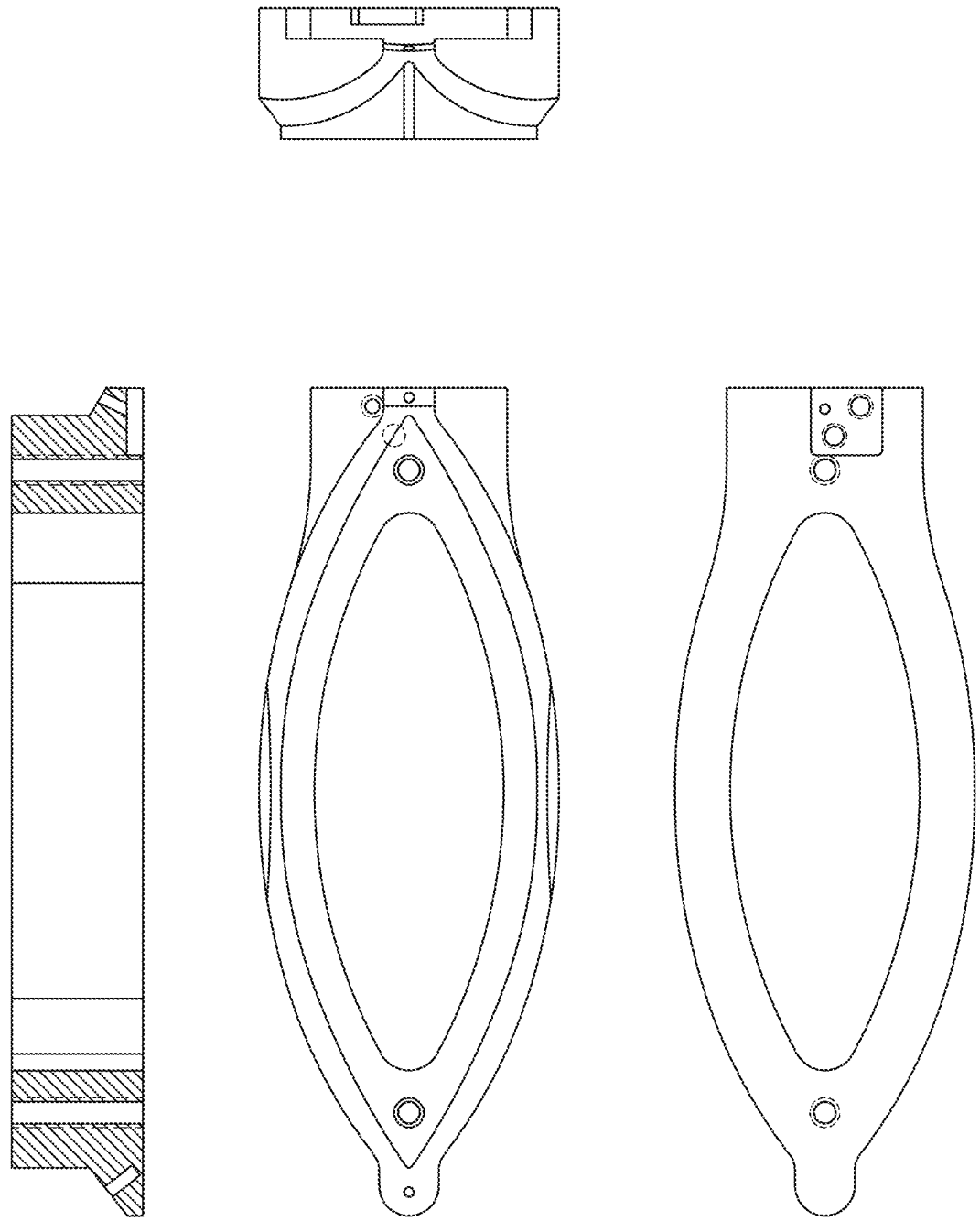
FIG. 30 shows a manufacturing component for forming a frame, as may be implemented in accordance with one or more embodiments.
Figure 32:
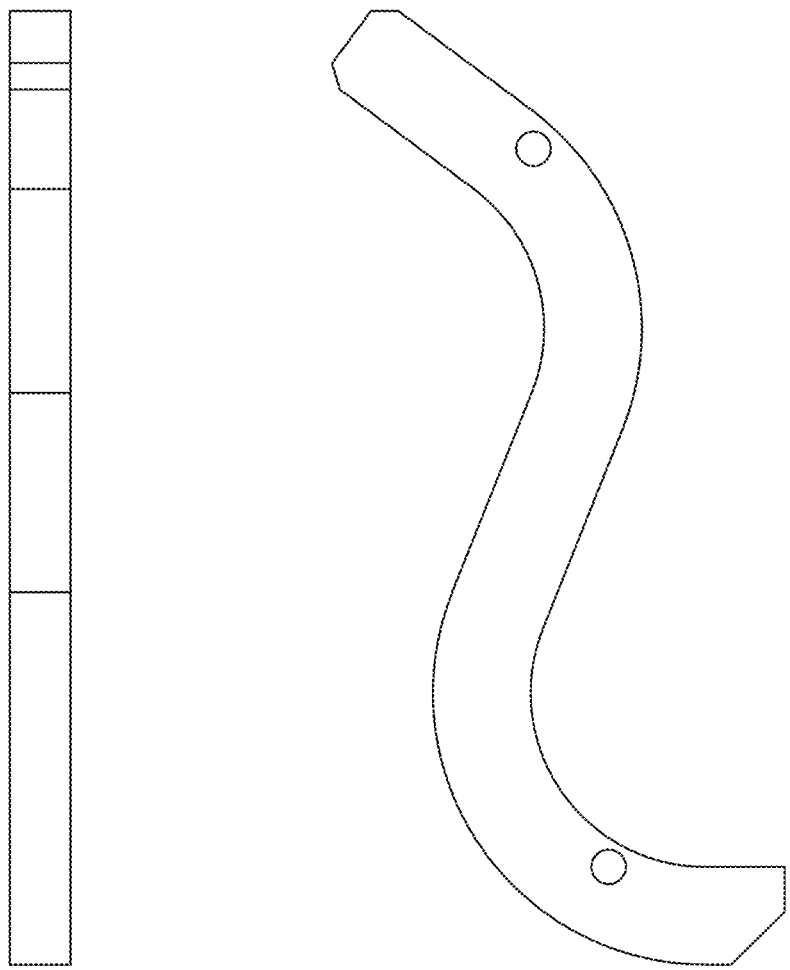
FIG. 32 shows a manufacturing fixture for forming an extension arm, as may be implemented in accordance with one or more embodiments.
Figure 33:
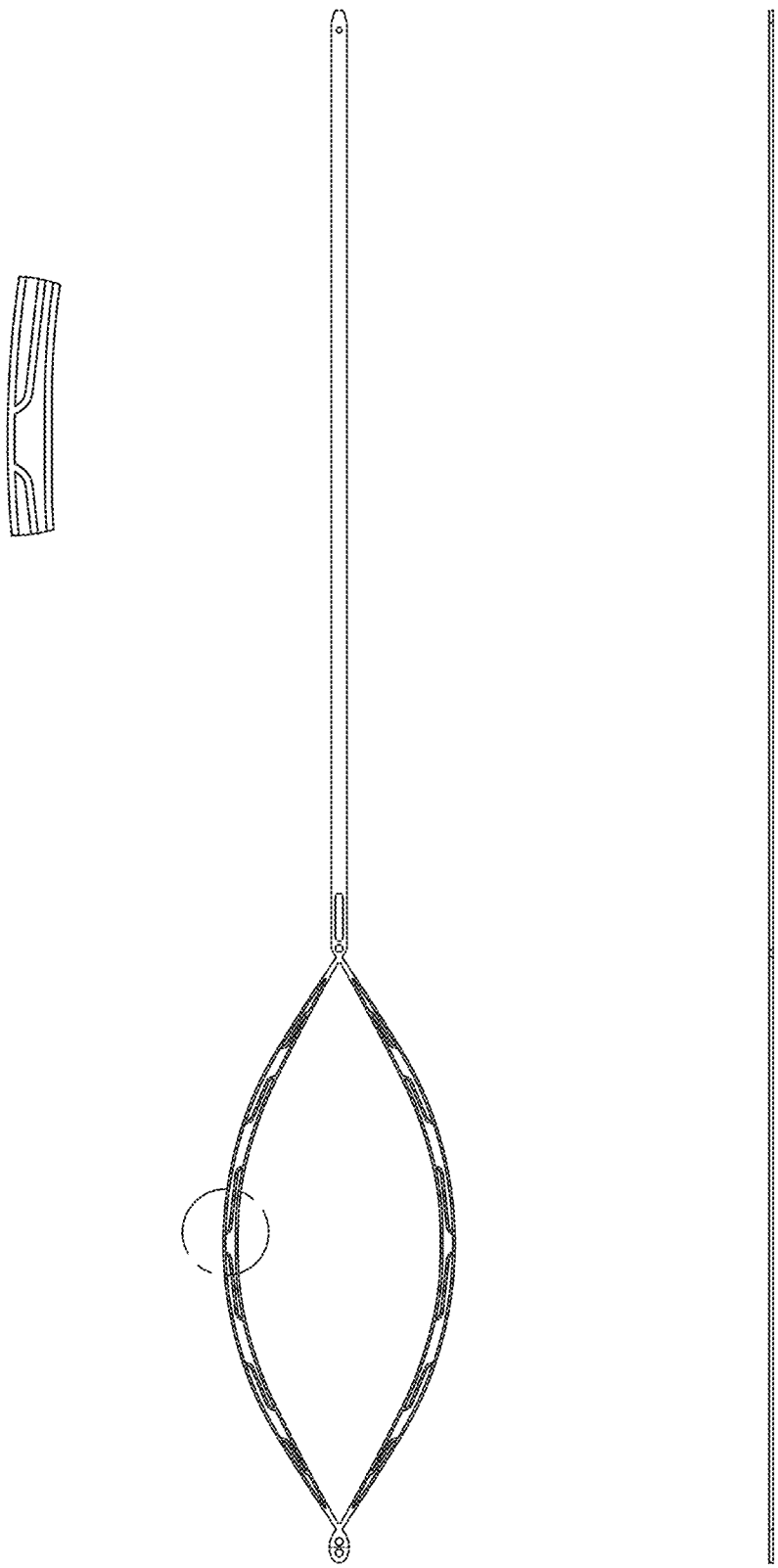
FIG. 33 shows an extension arm and frame, as may be implemented in accordance with one or more embodiments.

FIGS. 30, 31 and 32 show manufacturing components for forming a frame, as may be implemented in accordance with one or more embodiments. FIGS. 30 and 31 show respective aspects of a fixture (e.g., lower/upper portions relative to FIG. 28) that may be implemented together for frame formation, and FIG. 32 shows a curved portion that may be implemented with an extension arm. FIG. 33 shows an extension arm and frame in a planar state, as may be implemented in accordance with one or more embodiments.

FIG. 34 shows views and various cross-sections for an apparatus including aspects for formation of an extension arm. FIG. 35 shows a manufacturing fixture, as may be implemented in accordance with one or more embodiments for supporting one or more aspects for frame and extension arm manufacture, as may be implemented in accordance with one or more embodiments.

Consistent with one or more embodiments, a filter apparatus mitigates or prevents embolus from traveling into the great vessels (Brachiocephalic/Innominate, Left Common Carotid, and Left Subclavian arteries), and may be implemented during surgery from the aortic arch, which is the portion of the main artery that bends between the ascending and descending aorta. The aortic arch leaves the heart and ascends, then descends back to create the arch. The aorta distributes blood from the left ventricle of the heart to the rest of the body, and exhibits variable flow characteristics, with hemodynamics of the aortic arch region often exhibiting a non-uniform distribution of pressure and velocity. Particles such as embolus can be filtered under such conditions, using a filter component that conforms to the variable geometry of the aortic arch during cyclic pressure variations, functioning as a filtering umbrella. The collected emboli is extracted and removed through a delivery tube to outside of the body, such as by collapsing and drawing the filter component into a sheath.

In a particular embodiment, a filter mechanism as noted above includes a main frame assembly (FA) and a mesh umbrella, attached securely to the frame. The frame and mesh may be integrated as a single piece/component or with two or more pieces/components. The FA operates to provide a mechanical seal about an opening in an inner wall of vascular tissue with the FA conformed to the wall. Accordingly, micro-emboli and other particulates can be prevented from entering the opening while allowing unrestricted blood flow within the vascular tissue to which the FA is conformed. In various implementations, the FA is operable to maintain the conformity and mechanical seal under variations in cyclic blood pressure for humans under various conditions including those involving surgery, and for various anatomies and conditions such as those involving variations in aortic arch diameter and/or size or the accumulation of plaque. For instance, a mesh may be deployed with an area that is at least twice as large as any opening or openings to be covered. As such, various aspects of the FA may be implemented to facilitate such capture during surgery via catheter deployment, with FA being operable to collapse/trap particulates such as micro-emboli and withdraw the particulates into the catheter for removal upon completion of the surgery. Moreover, by controlling pressure via mechanical spring force, the application of too much pressure can be avoided, as may be useful for instances in which vessel wall stiffening or aneurism may be present.

According to another example embodiment, an apparatus includes a catheter extending from a proximal end to a distal end, a shaft within and operable to move in the catheter, and a filter component connected to an end of the shaft and operable to extend from and retract within the distal end of the catheter. The filter component includes a mesh and inner and outer frames connected by struts, with the mesh is coupled to one or both of the inner frame and the outer frame. The outer frame extends along the inner frame (e.g., in a concentric type arrangement). The struts operate to apply a force between the outer frame and the inner frame, along a direction generally between the frames (tending to push the frames away from one another). The frames may be oval, round or rectangular, with the latter approach facilitating the implementation of a flat surface for applying pressure to tissue. One or more of the mesh, frames and struts can be made of a contiguous material. In various embodiments, the struts apply a force that presses the inner frame and mesh against tissue, such as against an inner region of vascular tissue. Brush-like structures can be used in a perimeter region to facilitate sealing.

As noted herein such approaches can be particularly useful for deploying the mesh against an inner wall of the aortic arch, sealing the mesh around one or more artery openings therein. Deployment may involve, for example, constraining movement of the filter assembly to rotational movement, via the catheter/shaft, which facilitates the application of pressure to the mesh against tissue walls. Further, these approaches can facilitate insertion and filtering while conforming nearly all of the mesh and supporting structure to a sidewall of the aortic arch, allowing blood to flow freely therein while also capturing particles that may otherwise enter the covered artery or arteries. For instance, human red blood cells can be passed while mitigating passage of particles having a dimension larger than the human red blood cells. These particles can be trapped within the mesh/frames such that they can be withdrawn without allowing the particles to further escape back into the bloodstream.

The mesh can be sealed to an interior vessel wall or other tissue in a variety of manners. In some embodiments, the struts operate with the inner frame, outer frame and mesh to, in a deployed state, seal a perimeter region of the mesh to an interior vessel wall by using an applied force to press the mesh perimeter region onto the interior vessel wall. This may involve, for example, applying a force along various struts and between different adjacent regions of the inner and outer frames, such that a distance between the frames varies relative to conformity of one or both frames to tissue anatomy. This flexibility allows the application of sufficient sealing force along the perimeter region, while also accommodating anatomical differences.

In various implementations, the mesh has opposing surfaces and is configured and arranged with the shaft, frames and struts to conform to an inner wall of vascular tissue and cover at least one opening in the vascular tissue. Substantially all of one of the opposing surfaces can be placed in contact with the wall or extending over the at least one opening. This facilitates placement of the mesh predominantly out of the flow of blood in the vascular tissue.

Deployment of the mesh, in these and other contexts, can be effected by the filter component, shaft and catheter by expanding the mesh in a first state in response to the filter component being extended out of the distal end of the catheter, and collapsing the mesh in a second state in response to the filter component being retracted into the catheter. Accordingly, the mesh can be collapsed for fitment into the catheter and expanded upon deployment with a much wider coverage for filtering (e.g., two or many more times the diameter of the catheter).

Forces may be translated the filter component in a variety of manners. In some embodiments, the filter component includes a mechanical spring coupled at the distal end of the shaft. The mechanical spring operates with the shaft and catheter as a base, to apply a spring force that directs the mesh against tissue. For instance, the mechanical spring may operate with the catheter and shaft to apply a spring force to the outer frame in a direction toward the inner frame, with the force being translated from the outer frame to the inner frame via the struts. In some implementations, the spring directly applies a force to the inner frame. The spring may be separate from, or integrated with, a support structure connecting the filter component to the shaft (or as part of the filter component). Such approaches can be used to apply the catheter within a human aortic arch, sealing the mesh to an inner wall of the aortic arch and therein covering at least one opening in the human aortic arch with mesh.

Mesh or other filter material as characterized herein may be implemented in a variety of manners. In some embodiments, a mesh includes a stiffening structure and is operable to fold and unfold in overlapping layers, respectively for retraction into the catheter and for deployment. The stiffening structure may, for example, include additional material on or in the mesh and regions that exhibit lower stiffness for folding. For instance, the mesh may be patterned with differently-sized pores and/or with pore density that facilitates longitudinal or lateral folding/stacking behavior. A spiral pattern can facilitate certain opening or closing behaviors. Areas with fewer or no pores can be implemented to induce a stiffening moment.

Referring back to FIG. 1, an apparatus 100 is shown, as may be implemented for supporting a filter or mesh, in accordance with one or more example embodiments. The apparatus 100 includes an inner frame 110 and an outer frame 120 coupled by a struts 130 which operate to apply a force that pushes the inner and outer frame apart. A proximal end 140 is operable for coupling to a shaft, and is coupled to a distal end 150 via the frames. By way of example, the distal end 150 is shown extending at an angle relative to the inner frame 110, which can facilitate placement within a vessel wall (e.g., with the inner frame 110 pressed onto an inner wall within the aortic arch). Such an angle may facilitate placement of the apparatus into the aortic arch with the distal end 150 avoiding intervention into arteries in the walls. In certain implementations, a covering such as a thermoplastic show may be placed over the distal end 150 and facilitate interaction with vascular tissue.

In certain implementations, the proximal end 140 includes a mechanical spring (e.g., which may be integrated within the structure shown), that provides an upward (as depicted) spring force that can also facilitate pressing of the inner frame 110 against an inner wall of a vessel. For instance, with the proximal end 140 coupled to a shaft and inserted into vascular tissue via a catheter, the shaft and proximal end 140 can apply a spring force that tends to push the inner frame 110 upward and against an interior wall of the vascular tissue. Such an approach is particularly useful, for example, within an aortic arch. In some instances, both the frames are pressed against the inner wall of the vascular tissue. With a mesh coupled across the perimeter of the inner frame 110 (and, in some instances, across an overlying perimeter of the outer frame 120), blood flowing through openings in the inner wall within the perimeter of the inner frame is thus filtered via the mesh. Such a mesh may, for example, be implemented with a structure as shown at 160 (partially shown, with such a mesh filling the entire interior area within the perimeter of the inner frame 110). Moreover, a spring force in the proximal end 140 can be used to maintain a seal against a vessel wall under various blood flow conditions and for various anatomies.

In various implementations, mechanical force applied via such a spring and/or the struts 130 may be implemented as a primary force that conforms the structure against the inner wall (e.g., with a mechanical force that is many times larger than fluidic force of blood passing through a vessel). This force may be tuned, for example, during a manufacturing process to tailor the application to a particular use. For instance, the force can be scaled based on a patient's age and condition of the wall against which the mesh is to be deployed, such as may relate to size or the presence of plaque. Controlling an adherence force can facilitate optimization of the size of the mesh, such that the mesh need not be oversized to compensate for any such force.

The apparatus 100 may be made of one or more components. In some embodiments, the inner frame 110, outer frame 120 and struts 130 are formed of a contiguous material, eliminating any need for joints. In various implementations, a mesh (e.g., 160) coupled across the inner frame 110 is also formed with at least the inner frame of a contiguous material. For example, a contiguous nitinol material may be used to form one or all of the components in the apparatus 100. In some embodiments, a thin thermoplastic material is used a mesh and coupled to the inner frame. Where two components are used, they may be joined together using joining methods involving one or more of heat and pressure, adhesive, and lasers. The frames and struts can also be made using polymeric material and/or metallic material. The mesh can be attached directly to the frames and/or to itself.

In various embodiments, a mesh such as mesh 160 includes brush like teeth and grooves that enhance the grip of the mesh over rough terrain (e.g., over the surface of the aortic arch). These brush features may be located in the area of the frames. Small features such as microfeatures (relative to the vessel wall structures) receive the spring force and are highly compressible against the vessel, therein sealing against the vessel.

In various implementations, the apparatus 100 is operable to keep tissue under tension (e.g., along and into the interior of vascular tissue) when the inner and outer frames 110/120 are deployed. In this context, enough sealing pressure is applied to maintain the structure sealed against the wall under conditions in which blood is flowing past and through the mesh. This involves providing a smooth surface of interaction along an interface between the apparatus and the surface of the tissue (e.g., of the aortic arch). Such an approach can be implemented with few or no bumps or raised sections due to welding, bonding, overlap, and reducing/minimizing features such as "gutters," thus facilitating a tight seal with the vascular tissue.

Figure 2:
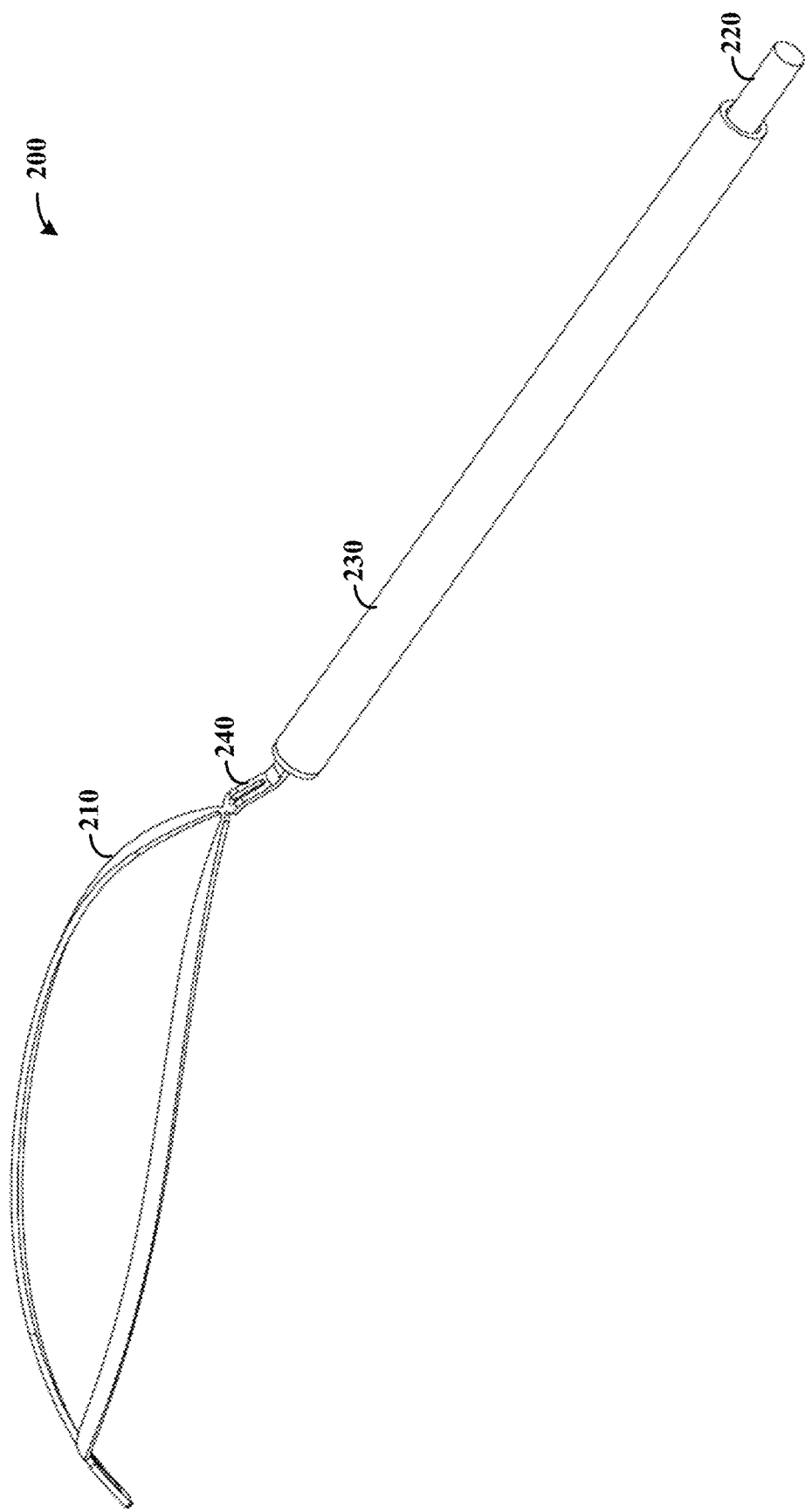
FIG. 2 shows a catheter apparatus, in accordance with one or more example embodiments of the present disclosure.

FIG. 2 shows an apparatus 200, in accordance with one or more example embodiments of the present disclosure. The apparatus 200 includes a filter component 210, which may be implemented with inner and outer frames with connecting struts as shown in FIG. 1. The filter component is connected to a shaft 220 that extends through a catheter 230 (e.g., with the shaft and catheter being many times longer than the portions shown). A proximal end 240 of the filter component 210 is secured to the shaft 220 and provides a spring force an in upward direction as depicted in the figure, sealing a perimeter of the filter component 210 against a vessel wall when deployed therein.

FIGS. 3A-3D show respective views of an apparatus 300, in accordance with one or more example embodiments of the present disclosure. As shown in FIG. 3A, the apparatus 300 includes a filter component 310 coupled to a shaft 320 within a catheter 330, with the filter component being retractable into the catheter. A mesh may be coupled to and/or integrated with the filter component 310, across respective rails (e.g., as shown in FIG. 1). FIG. 3B shows a cross-sectional view "A-A" from FIG. 3A, with FIG. 3C showing a view of a distal end of the catheter and shaft as coupled to a proximal end 340 of filter component 310. In various implementations, a portion of the proximal end 340 is locked in place onto the shaft 320 such that it does not extend beyond end 350 of the catheter 330. This maintains componentry within the catheter and out of the bloodstream when deployed in vascular tissue. FIG. 3D shows an alternate view of the apparatus 300.

In various implementations, a portion of the proximal end 340 is locked in place onto the shaft 320 such that it does not extend beyond the end of the catheter 330. This maintains componentry within the catheter and out of the bloodstream when deployed in vascular tissue.

Figure 4:
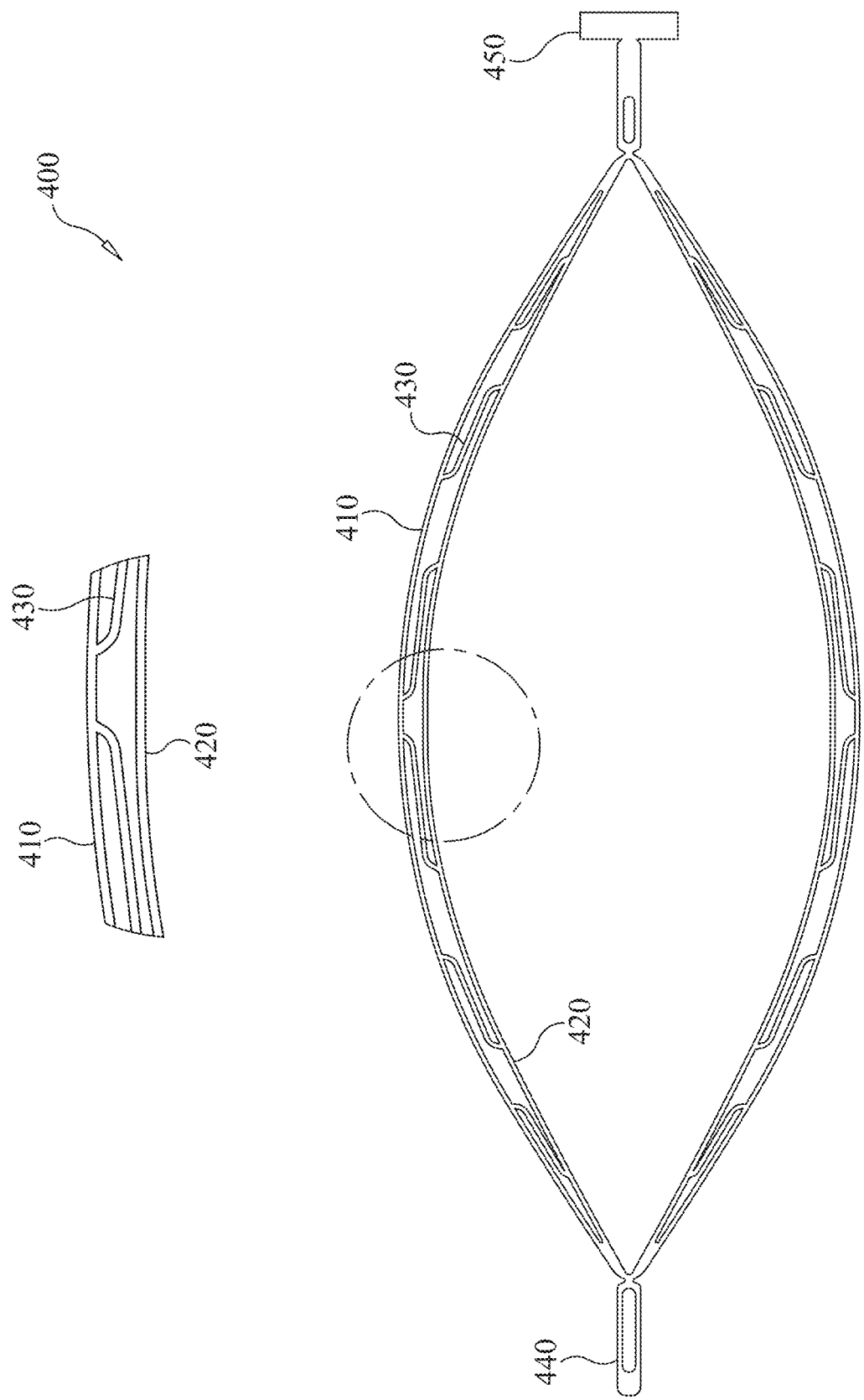
FIG. 4 shows a filter support apparatus, in accordance with one or more example embodiments of the present disclosure.

FIG. 4 shows an apparatus 400 as may be implemented to support a mesh or filter, in accordance with one or more example embodiments of the present disclosure. The dimensions shown in FIG. 4 are exemplary, as may be implemented for certain embodiments. The apparatus 400 includes an inner frame 410, outer frame 420 and struts 430 that push the frames apart. Detail "A" provides an exemplary view of these components. A distal end 440 and proximal end 450 are coupled to the frames as shown.

Figure 5:
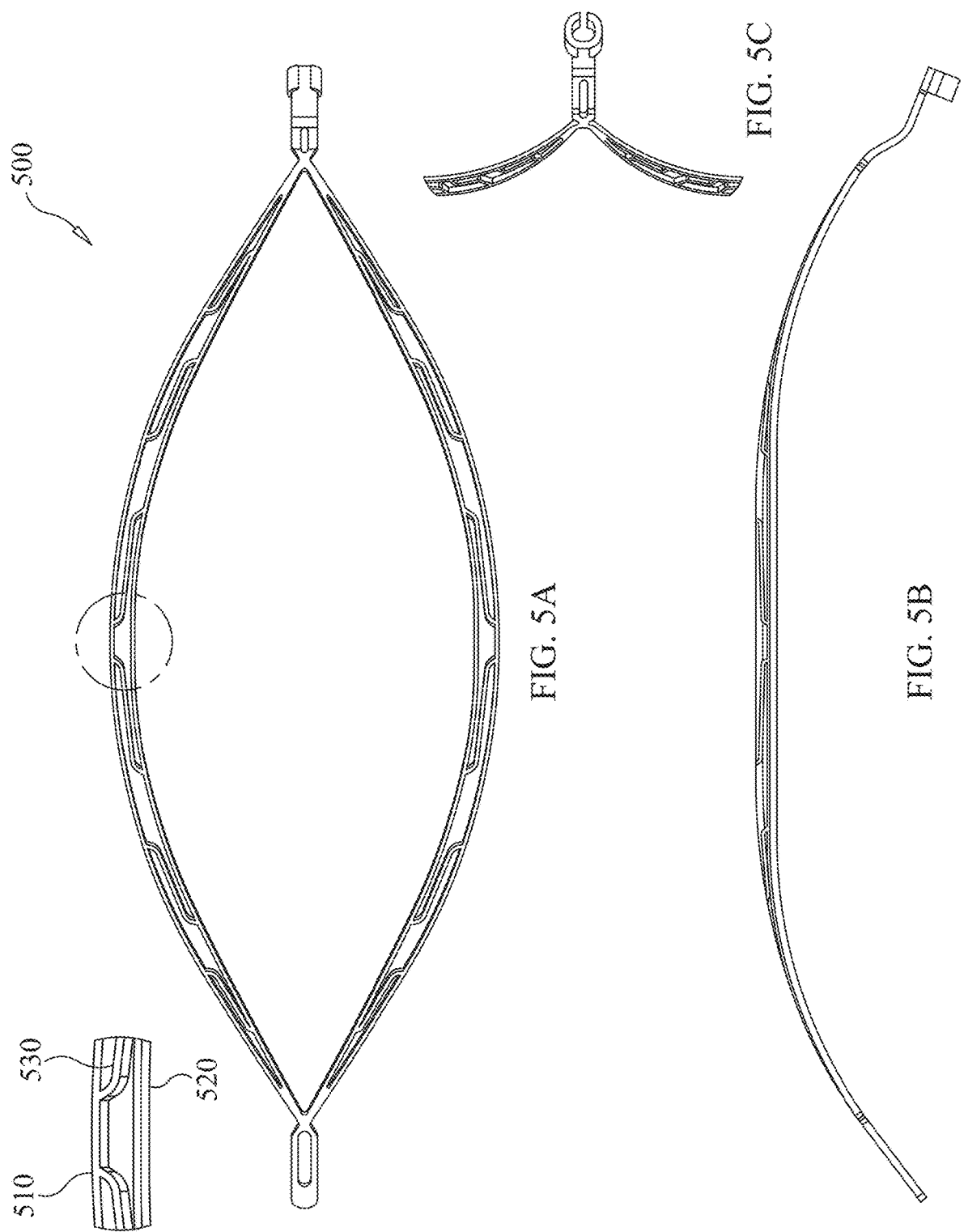
FIGS. 5A-5C show respective views of a filter support apparatus, in accordance with one or more example embodiments of the present disclosure.

FIGS. 5A-5C show respective views of an apparatus 500 as may be implemented to support a mesh or filter, in accordance with one or more example embodiments of the present disclosure. The apparatus 500 may be implemented similarly to that shown in FIG. 4. As noted in the detail portion "A" of FIG. 5A, inner (510) and outer (520) frames are connected by struts 530 that push the inner frame away from the outer frame and onto a vessel wall. FIGS. 5B and 5C respectively show side and end views of the apparatus 500.

Figure 6:
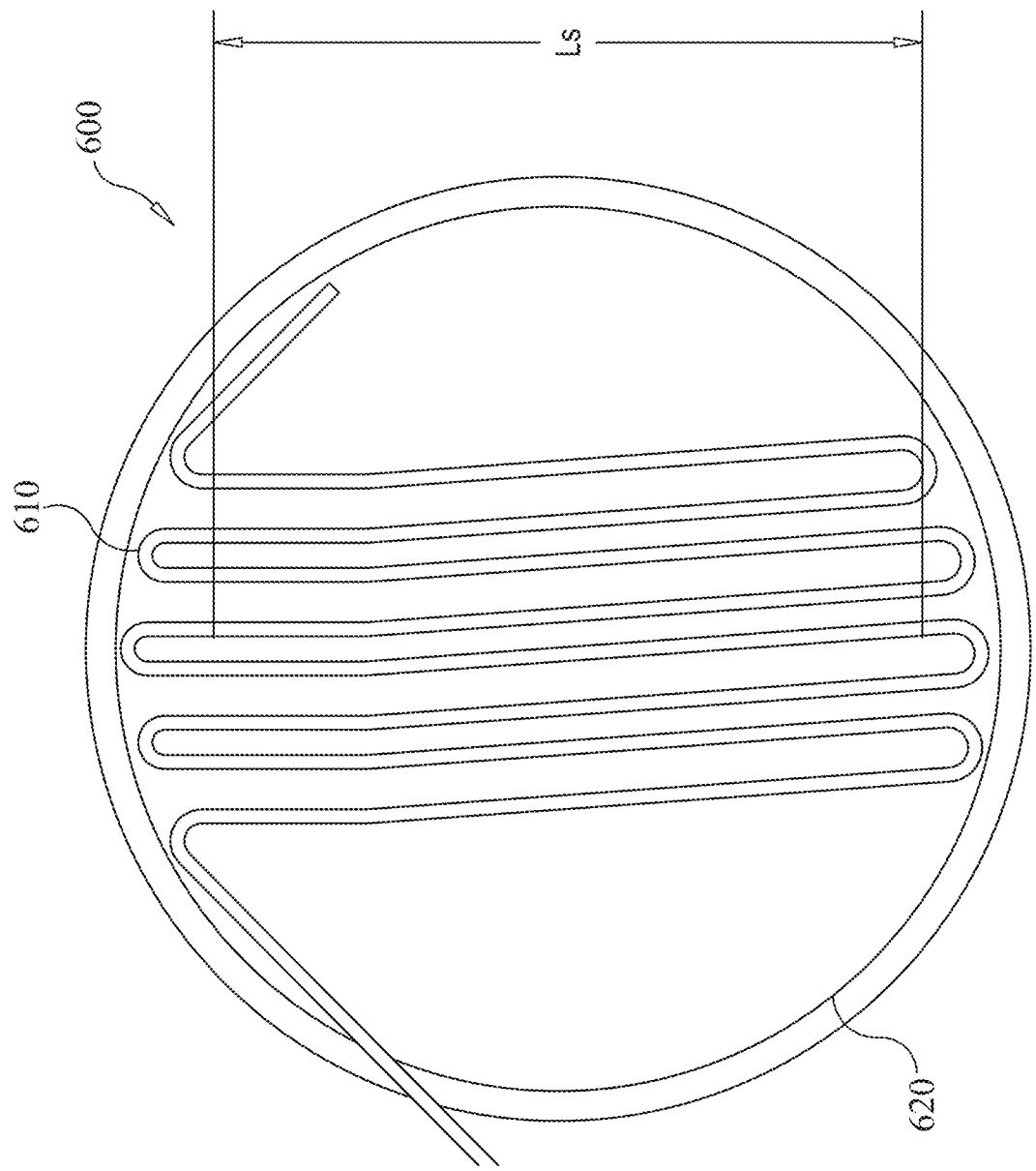
FIG. 6 shows a catheter apparatus with a retracted mesh, in accordance with one or more example embodiments of the present disclosure.

FIG. 6 shows a catheter apparatus 600 with a retracted mesh 610 within a sheath 620, in accordance with one or more example embodiments of the present disclosure. The mesh 610 may, for example, be implemented with filter components as shown in FIGS. 1 and 2, and operable for folding and retraction into a catheter. For instance, after deployment upon a an inner wall of the aortic arch and use for filtering particulates from blood flowing into arteries sealed by the mesh 610, the mesh can be folded and retracted into the sheath 620 as shown to trap and remove the particulates. In various implementations, the mesh 610 has stiffening/ribs structure which enables it to fold and unfold in certain desired direction when it is deployed or retracted within the sheath 620.

Figure 7A:
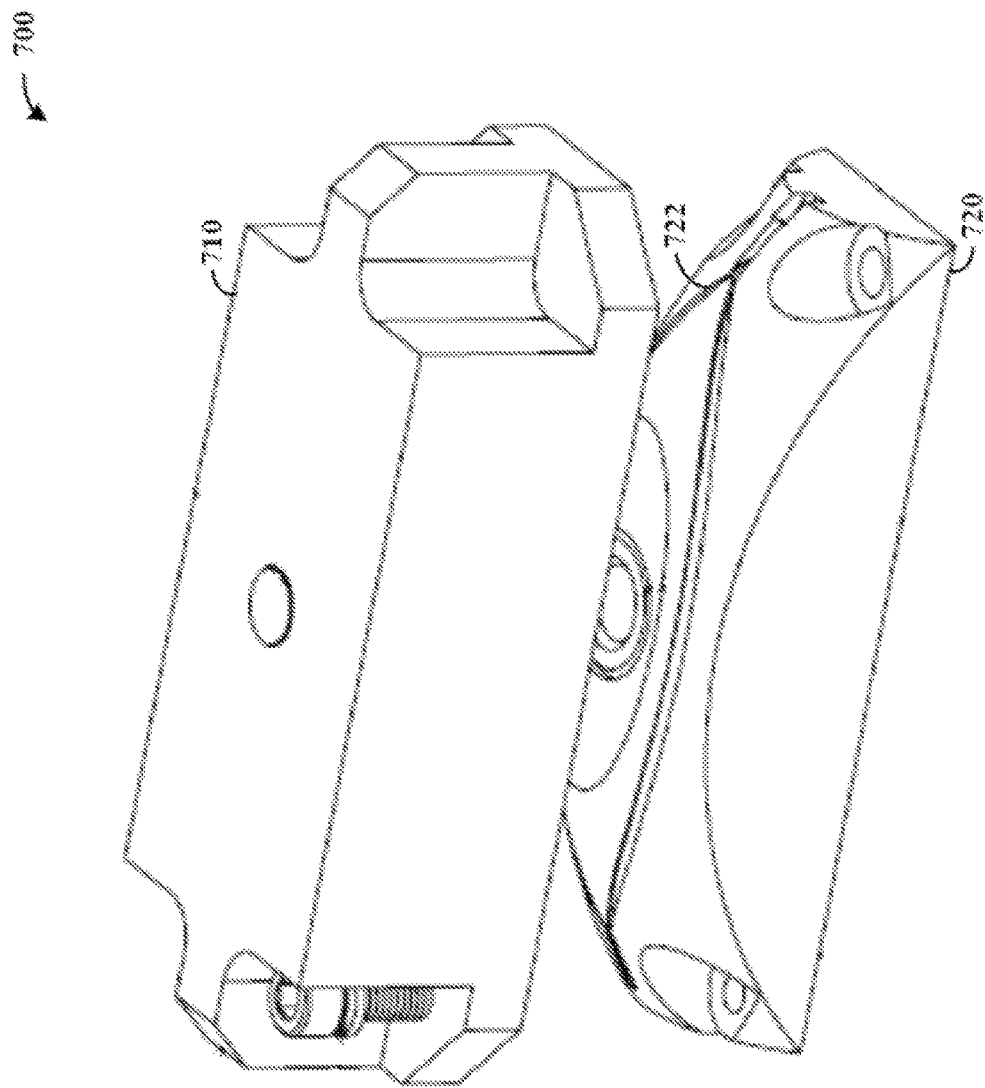

FIGS. 7A-7G show respective views of a filter support manufacturing apparatus 700, as may be implemented in accordance with one or more example embodiments of the present disclosure. The respective dimensions shown are exemplary, with the understanding that the apparatus 700 may be built to a variety of dimensions. The apparatus 700 may, for example, be used to manufacture one or more filter components as shown in other figures herein. Referring to FIG. 7A, an upper fixture 710 and lower fixture 720 are shown in perspective view, with a formed region 722 shown on the lower fixture and operable for forming a filter component.

FIGS. 7B and 7C respectively show end and top views of the apparatus 700, with the upper and lower fixtures 710 and 720 positioned in a forming stage. Section A-A from FIG. 7B is also shown with a region 730 providing a space between the upper and lower fixtures 710/720 for forming the filter component. Such an approach can be facilitated for a variety of molding approaches.

Figure 7D:
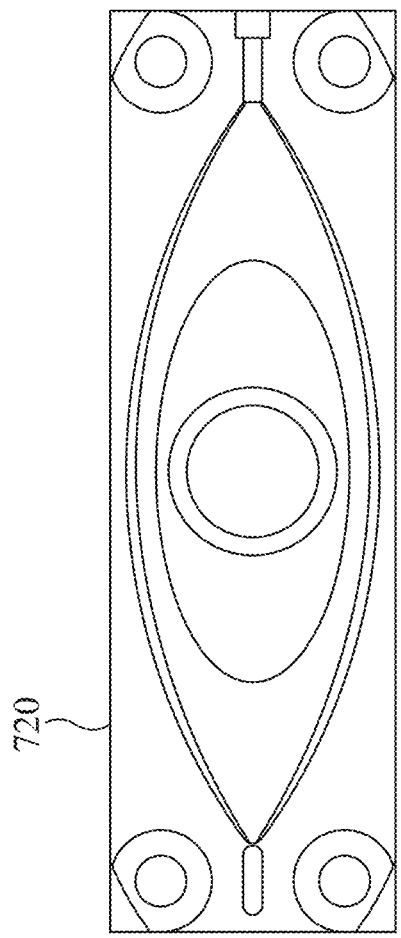
Figure 7E:
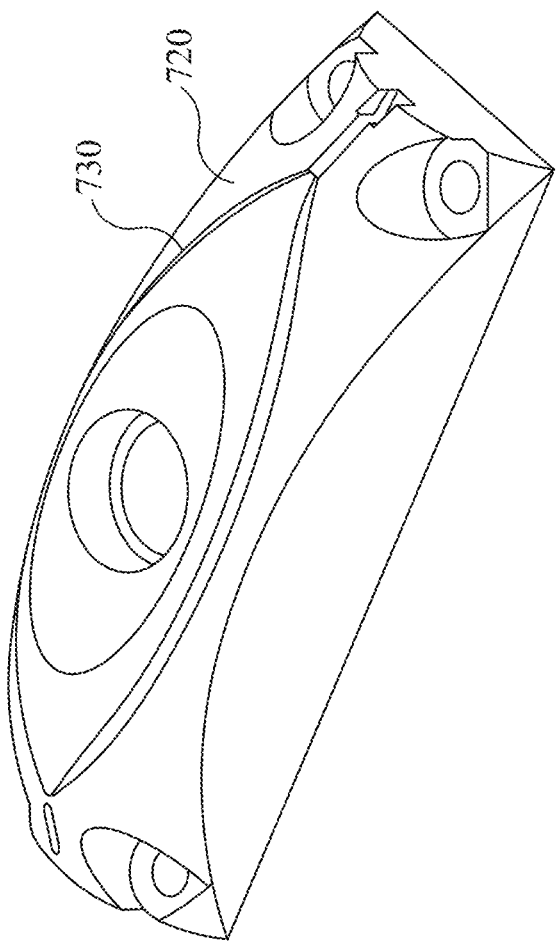

FIG. 7D and FIG. 7E respectively show top and perspective views of the lower fixture 720. As part of FIG. 7D, sections A-A, B-B, D-D and detail C are shown for various cross sections and related detail. Region 730 is recessed for forming part of a filter component.

Figure 7F:
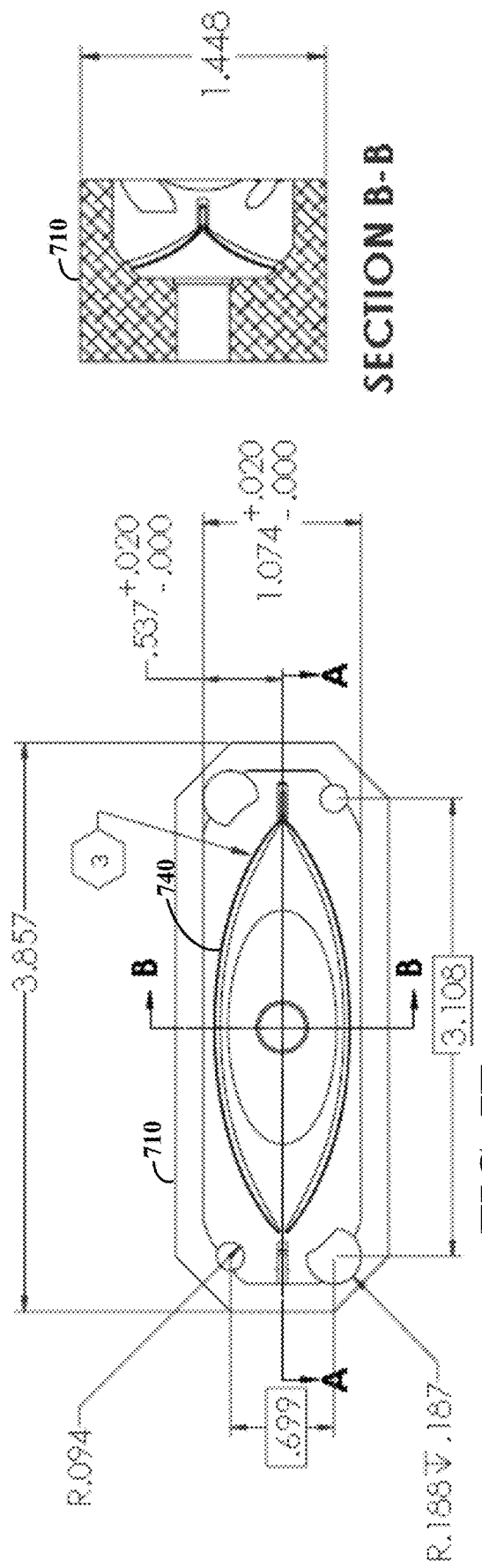
Figure 7G:
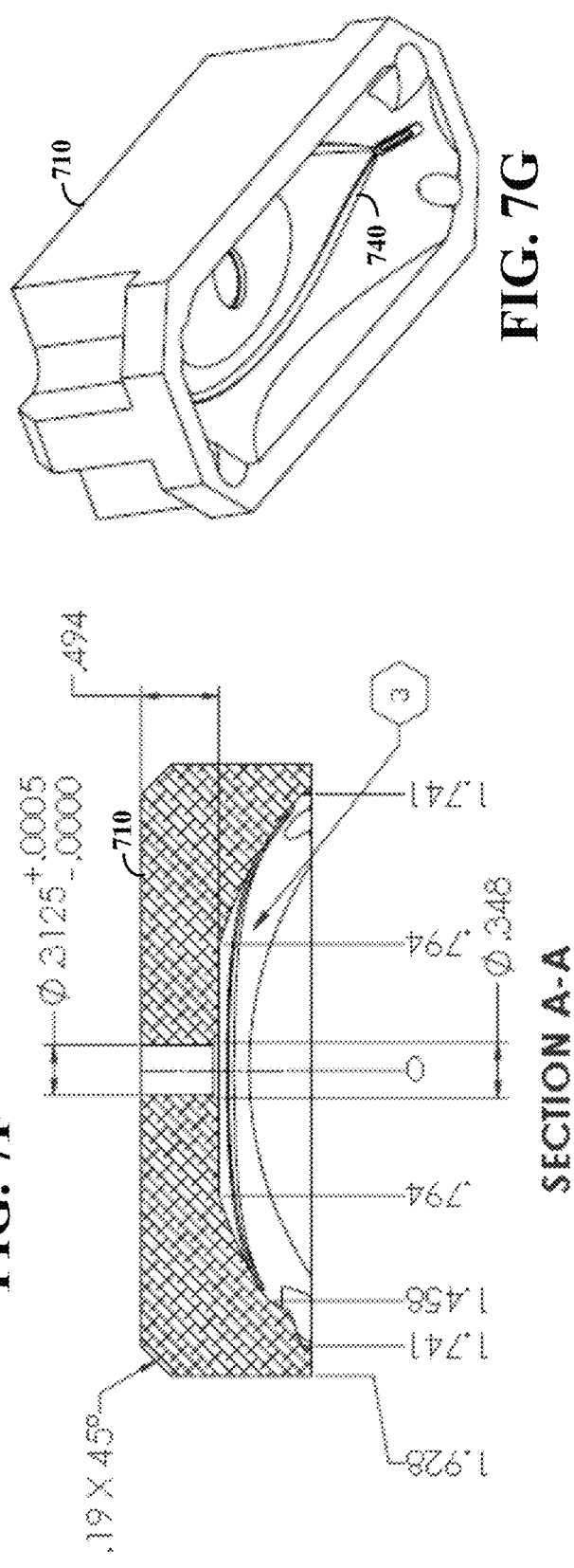

FIG. 7F and FIG. 7G respectively show top and perspective views of the upper fixture 710. As part of FIG. 7F, sections A-A and B-B are shown for respective cross sections. Region 740 is recessed for forming part of a filter component.

Various other approaches to manufacturing may be implemented to suit particular embodiments. In some embodiments, a starting material is processed to generate a mesh. For example, in some instances a flat nitinol material is used, in which a mesh area is first reduced to less than 0.005" (or less than 0.001") using electro-discharge machining (EDM) or other technique. The frame assembly and mesh patterns are then cut using for example a laser. In some instances, the order of process is reversed such that a frame assembly (frames) are laser cut followed by EDM and laser patterning.

In various embodiments, a frame assembly such as may be implemented with the frame/mesh supporting components shown in one or more of FIGS. 1-5C has a rectangular cross section that provides directional stiffness and also higher force relative to a circular cross section. The rectangular cross section provides a desirable surface contact area and more distributive force, which facilitates sealing. The flat and rectangular frame structure can be implemented with a double frame and struts to keep tissue under tension (no sagging) in both lateral and axial directions. This can facilitate uniform fluid pressure on the mesh and artery openings in the tissue.

Figure 8:
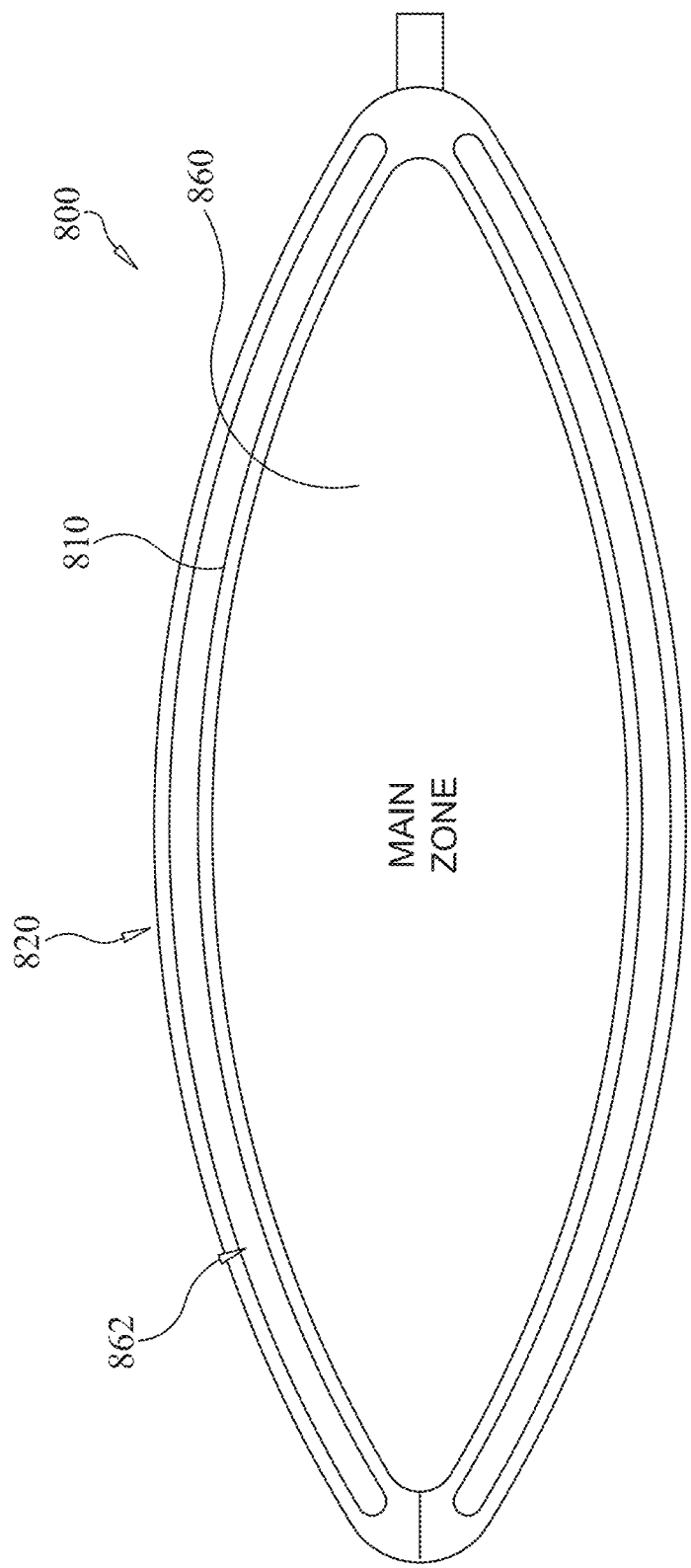
FIG. 8 shows a filter component, as may be implemented with various embodiments.

Referring to FIG. 8, an apparatus 800 is shown, as may be implemented with various embodiments involving filtering. The apparatus 800 includes inner and outer frames 810 and 820, and a mesh 860 that covers a main zone within a perimeter defined by the inner frame and in a region 862 between the inner and outer frames. In various embodiments, two mesh layers are implemented, with a first mesh having a perimeter that aligns with the perimeter of the inner frame 810 a second mesh overlying the first mesh and having a perimeter that aligns with the perimeter of the outer frame 820. In various embodiments, the inner frame 810 and outer frame 820 are operable for pressing against the inner wall of vascular tissue, forming a flat or double seal for filtering blood flowing through an artery in the inner wall. The apparatus 800 may also be implemented with struts between the inner and outer frame, such as shown in FIG. 4.

In various embodiments, a frame assembly is designed to provide spring constant(s) of frame assembly with double flat seal around the main zone. This can increase the reliability of the sealing, provide increased contact force to interior walls of tissue (e.g., aorta) and more adhesion/bonding force between the tissue and the layers. The frame structure may be implemented with spring componentry that facilitates deployment and collapse of the mesh. The frame assembly may be made of four layers to support forces for sealing, deployment, lateral, twisting, pull-in, and constraint. These aspects may, for example, be implemented with the apparatus 800 in FIG. 8 as well as other filter componentry as shown in the other figures.

Figure 9:
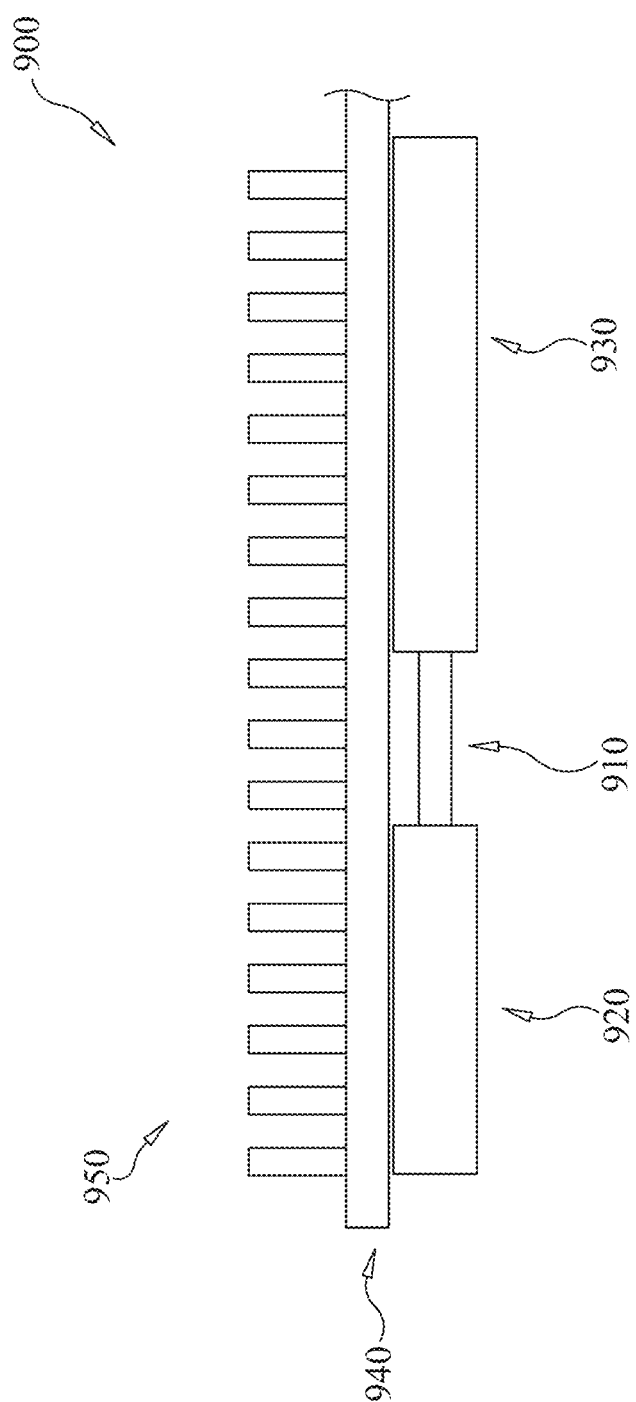
FIG. 9 shows brush features of an apparatus as may be implemented with one or more embodiments.

FIG. 9 shows brush features of an apparatus 900 as may be implemented with one or more embodiments. For instance, the features shown in FIG. 9 may be implemented with the mesh 160 in FIG. 1. The apparatus 900 includes inner and outer frames 910 and 920, coupled by struts 930 that tend to push the frames away from one another. A mesh 940 (a portion shown) is coupled to the frames and brush-like features 950 are coupled to the mesh near the frames. The frames 910 and 920 together with the struts 930 apply pressure to the mesh 940 and to the brush-like features 950 in an upward direction as depicted in the figure, such as for sealing the mesh to an inner wall of vascular tissue (e.g., over an surface of the aortic arch). The brush-like features 950, which may be formed of a common material with the mesh 940, are compressible for facilitating sealing of the mesh against an inner wall.

Based upon the above discussion and illustrations, those skilled in the art will readily recognize that various modifications and changes may be made to the various embodiments without strictly following the exemplary embodiments and applications illustrated and described herein. For example, different types of materials may be used for the various components herein, and other manners in which to expand/collapse mesh-type structures with similar effect can be implemented. Additional and/or differently-shaped frame portions or struts may be used to tailor the application to particular anatomies. In addition, the various methods described herein may be implemented with different types of arteries, valves and tissue, as well as different types of live beings. Such modifications do not depart from the true spirit and scope of various aspects of the invention, including aspects set forth in the claims.

What is claimed is:

1. An apparatus comprising:
   an extension arm;
   a frame connected to the extension arm; and
   a filter having opposing surface areas terminating around a perimeter of the filter, the filter being connected to the frame at the perimeter and configured and arranged with the frame and the extension arm to:
   expand with the frame in a deployed state, and
   in the deployed state, conform one of the opposing surface areas to an inner sidewall of a tubular organ in response to force applied to the extension arm in a first direction along a length thereof toward respective surfaces of the inner sidewall of the tubular organ, by engaging the extension arm with the respective surfaces of the inner sidewall of the tubular organ and using the respective surfaces to redirect the applied force in a direction extending toward the frame, therein sealing the frame and the perimeter of the filter to the inner sidewall.

2. The apparatus of claim 1, further including a shaft connected to the extension arm and configured and arranged to:
   slide within a catheter;
   apply the force to the extension arm in the first direction; and
   position the extension arm, frame and filter relative to the inner sidewall of the tubular organ for applying the force to the frame.

3. The apparatus of claim 2, further including the catheter, wherein the shaft is configured and arranged with the frame to collapse the frame and the filter into a collapsed state, and to withdraw the frame and filter into the catheter in the collapsed state.

4. The apparatus of claim 3, wherein the shaft is configured and arranged with the frame to, via collapse of the filter, trap particles trapped on the other one of the opposing surfaces that is opposite the one of the opposing surfaces conformed to the inner sidewall, and to withdraw the trapped particles into the catheter for removal from the tubular organ.

5. The apparatus of claim 1, wherein the frame and extension arm are configured and arranged to collapse into a collapsed state and, in the collapsed state, retract into a catheter for withdrawal from the tubular organ.

6. The apparatus of claim 1, wherein the frame includes an inner frame configured and arranged for sealing the filter to the inner sidewall, an outer frame, and a plurality of struts that connect the inner frame to the outer frame and that are configured and arranged to translate force, applied via the extension arm to the outer frame, to the inner frame and therein flexibly conform the inner frame to the inner sidewall.

7. The apparatus of claim 6, wherein each of the plurality of struts extends lengthwise from a first end connected to and terminating on the inner frame, to a second end connected to and terminating on the outer frame, and wherein the struts are configured and arranged to facilitate flexure of the inner frame, relative to the outer frame, by providing a spring force and therein facilitate conformance of the outer frame to physical features of the inner sidewall.

8. The apparatus of claim 6, wherein
   the filter extends within a perimeter of the inner frame and between the inner frame and the outer frame, and
   the struts are configured and arranged to apply a force between the outer frame and the inner frame and seal an opening in an interior vessel wall by pressing the inner and outer frames against the interior vessel wall and around an opening therein.

9. The apparatus of claim 6, wherein the struts are configured and arranged to maintain the inner and outer frames at a displacement distance from one another that varies in accordance with the applied force.

10. The apparatus of claim 1, wherein the extension arm includes respective angulated segments extending longitudinally and connected with each other at respective ends of the angulated segments, and wherein the extension arm is configured and arranged to apply the force to the frame by applying a spring force that translates an input force applied along the length of the extension arm including the respective angulated segments, the input force having a force vector with a first direction toward one of the surfaces of the inner sidewall engaged by the extension arm, to an output force applied to the frame and having a force vector having a direction that extends away from the one of the surfaces of the inner sidewall.

11. An apparatus comprising:
   a catheter extending from a proximal end to a distal end and configured and arranged for insertion within a tubular organ;
   a shaft extending in the catheter from the proximal end to the distal end and being configured and arranged to move within the catheter;
   a frame connected to the shaft and configured and arranged with the shaft to retract into the catheter in a collapsed state and to extend out of the catheter in a deployed state; and
   a filter having opposing surface areas terminating around a perimeter of the filter, the filter being connected to the frame at the perimeter and configured and arranged with the frame to:
      expand with the frame in the deployed state and, in the deployed state, conform one of the opposing surface areas to an inner sidewall of the tubular organ, and collapse with the frame in the collapsed state; and
   wherein the shaft includes an extension arm configured and arranged with the frame and filter to, in the deployed state, engage with respective surfaces of the inner sidewall of the tubular organ in response to a force applied along a first length of the extension arm toward one of the respective surfaces of the inner sidewall and, via the engaging, redirect the applied force in a direction away from the one of the respective surfaces and toward the frame, therein sealing the frame and the perimeter of the filter to the inner sidewall.

12. The apparatus of claim 11, wherein the frame and filter are configured and arranged with the shaft and extension arm to, in response to being deployed within a human aortic arch in the deployed state,
   seal the perimeter of the filter around an arterial opening in the inner sidewall of the human aortic arch by applying the force to the frame and therein conforming the filter to the inner sidewall, and
   filter blood flowing through the arterial opening.

13. The apparatus of claim 11, wherein the extension arm is configured and arranged to apply the force to the frame by applying a spring force that translates an input force applied to the extension arm via the shaft, the input force having an input force vector with a first direction toward one of the respective surfaces with which the extension arm is engaged, to an output force applied by the inner sidewall and the extension arm to the frame, the output force having an output force vector extending a direction away from the one of the respective surfaces.

14. The apparatus of claim 11, wherein the frame and extension arm are configured and arranged with the shaft and catheter to trap particles on a surface area of the filter by collapsing into the collapsed state and, in the collapsed state, retracting into the catheter for withdrawal from the tubular organ.

15. The apparatus of claim 11, wherein the frame includes:
   an inner frame configured and arranged for sealing the filter to the inner sidewall,
   an outer frame, and
   a plurality of struts that connect the inner frame to the outer frame and that are configured and arranged with the outer frame to translate force applied via the extension arm to the inner frame and therein flexibly conform the inner frame to the inner sidewall.

16. The apparatus of claim 11, wherein the catheter is configured and arranged for insertion into a human aortic arch, and the shaft is configured and arranged with the frame to conform the filter to an interior wall of the aortic arch and to cover an opening in the aortic arch leading into at least one artery, with the frame pressed against the interior wall of the aortic arch and around the at least one artery.

17. The apparatus of claim 16, wherein the shaft and frame are configured and arranged to conform the filter to the interior wall and to cover at least one opening therein, with substantially all of one of the opposing surfaces being in contact with the wall or extending over the at least one opening.

18. An apparatus for use with a catheter, the apparatus comprising:
   a filter having a frame, the frame forming a perimeter of the filter and separating opposing surfaces of the filter; and
   an articulated arm connected to the frame and configured and arranged to, when deployed within a tubular organ and in response to a force applied along a length of a first segment of the articulated arm toward an inner sidewall of the tubular organ, engage with the inner sidewall of the tubular organ and utilize the inner sidewall to redirect the force in a direction extending along a length of a second segment of the articulated arm and toward the filter, and using the redirected force to seal the filter to the inner sidewall.

19. The apparatus of claim 18, wherein the articulated arm is configured with respective struts, each strut forming one of the segments of the articulated arm and being configured and arranged with a stiffness that, when engaged with opposing portions of the inner sidewall, provides a spring force that seals the frame and the filter to the inner sidewall.

20. The apparatus of claim 19, wherein each strut is coupled by a U-shaped bend configured and arranged to provide the spring force in response to the struts coupled thereto being engaged with the opposing inner sidewall portions.

* * * * *